(12) United States Patent
Kiguchi et al.

(10) Patent No.: US 12,400,468 B2
(45) Date of Patent: Aug. 26, 2025

(54) PROGRAM GENERATION ASSISTING SYSTEM FOR ASSISTING GENERATION OF PROGRAM FOR ANALYZING CLINICAL TRIAL

(71) Applicant: Shionogi & Co., Ltd., Osaka (JP)

(72) Inventors: Ryo Kiguchi, Osaka (JP); Masakazu Fujiwara, Osaka (JP); Yoshitake Kitanishi, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 319 days.

(21) Appl. No.: 18/012,539

(22) PCT Filed: Jun. 22, 2021

(86) PCT No.: PCT/JP2021/023524
§ 371 (c)(1),
(2) Date: Dec. 22, 2022

(87) PCT Pub. No.: WO2021/261468
PCT Pub. Date: Dec. 30, 2021

(65) Prior Publication Data
US 2023/0267757 A1 Aug. 24, 2023

(30) Foreign Application Priority Data
Jun. 23, 2020 (JP) .................. 2020-108248

(51) Int. Cl.
*G06V 30/413* (2022.01)
*G06V 10/82* (2022.01)
(Continued)

(52) U.S. Cl.
CPC ............ *G06V 30/413* (2022.01); *G06V 10/82* (2022.01); *G06V 30/19093* (2022.01); *G06V 30/19173* (2022.01); *G16H 10/20* (2018.01)

(58) Field of Classification Search
CPC ........... G06V 30/413; G06V 30/19093; G06V 30/19173; G06V 10/82; G16H 10/20; G16H 50/70
See application file for complete search history.

(56) References Cited

U.S. PATENT DOCUMENTS

2020/0251188 A1* 8/2020 Will ................. G16H 10/60

FOREIGN PATENT DOCUMENTS

| CN | 111292821 | 6/2020 |
|----|-----------|--------|
| JP | 2002-58650 | 2/2002 |

(Continued)

OTHER PUBLICATIONS

Extended European Search Report issued Jun. 19, 2024 in corresponding European Patent Application No. 21829208.4.
(Continued)

*Primary Examiner* — Daniel G Mariam
(74) *Attorney, Agent, or Firm* — Wenderoth, Lind & Ponack, L.L.P.

(57) ABSTRACT

A system is provided to assist automation of programming for automatic generation of an analysis material prepared by analysis work in a clinical trial during pharmaceutical development. Using the format information, the layout information, and the image data of an image/table analysis plan, this program generation assisting system performs form pattern prediction by two approaches: micro rule-based prediction and macro CNN-based prediction. In addition, the program generation assisting system performs model data/variable prediction by using the format information and the layout information of the image/table analysis plan, an ADaM specification, and ADaM/variable association information, and presents a combination of the model data/variable prediction and the pattern prediction.

19 Claims, 24 Drawing Sheets

(51) Int. Cl.
    *G06V 30/19*     (2022.01)
    *G16H 10/20*     (2018.01)

(56) References Cited

FOREIGN PATENT DOCUMENTS

| JP | 2011-159176 | 8/2011 |
| JP | 2016-192085 | 11/2016 |
| JP | 2019-114152 | 7/2019 |
| JP | 2020-35036 | 3/2020 |

OTHER PUBLICATIONS

Nizar Bouguila et al., "Discrete data clustering using finite mixture models", Pattern Recognition, vol. 42, No. 1, pp. 33-42, Jan. 1, 2009.
Imon Banerjee et al., "Comparative effectiveness of convolutional neural network (CNN) and recurrent neural network (RNN) architectures for radiology text report classification", Artificial Intelligence in Medicine, vol. 97, pp. 79-88, Jan. 1, 2019.
Daiju Ueda et al., "Technical and clinical overview of deep learning in radiology", Japanese Journal of Radiology, vol. 37, No. 1, pp. 15-33, Dec. 1, 2018.
International Search Report issued Aug. 3, 2021 in International (PCT) Application No. PCT/JP2021/023524.
International Preliminary Report on Patentability dated Jan. 5, 2023 in International (PCT) Application No. PCT/JP2021/023524.
Stackhouse, Michael et al., "An Automated Macro to Compare Data Transfers", PharmaSUG 2018—Paper AD-13, Covance, Inc., pp. 1-12.
Lesueur, Dale et al., "Automate Clinical Trial Date Issue Checking and Tracking", PharmaSUG 2018—Paper AD-31, Regeneron Pharmaceuticals Inc., pp. 1-5.
Chen, Min et al., "A SAS® Macro Tool to Automate Generation of Define.XML V2.0 from SDTM Specification for FDA Submission", PharmaSUG2016—Paper SS08, Alkermes Inc., pp. 1-24.
Lapann et al., "Automation of ADAM Dataset Creation with a Retrospective, Prospective and Pragmatic Process", PRA International, Dec. 2013, pp. 1-6.
Wei, William et al., "Automation of STDM dataset integration and ADaM dataset formation", PharmaSUG 2018—Paper AD-32, Merck & Co, Inc., pp. 1-11.
Watson, Richann et al., "Automated Validation of Complex Clinical Trials Made Easy", PharmaSUG 2018—Paper BB-24, pp. 1-35.
Watson, Richann, "Check Please: An Automated Approach to Log Checking", PharmaSUG 2017 Paper TT06, pp. 1-12.
Qi, Lingjiao et al., "Automating SAS Program Table of Contents for Your FDA Submission Package", PharmaSUG 2019—Paper AP-298, Statistics & Data Corporation, pp. 1-14.
Williams, Valerie et al., "A Utility to Reconcile Report Numbers and Titles", PharmaSUG 2019—Paper AD-316, ICON Clinical Research, pp. 1-5.
Markway, Taylor, "SDTM Automation with Standard CRF Pages", SCRI Development Innovations, PharmaSUG 2016—Paper PO21, pp. 1-10.

\* cited by examiner

Fig. 3

Specific example of ADaM data set: ADEG

| Patient ID | Medication information | Analysis time point (week) | Test item name | Clinical test value | Comment | ← Variable information |
|---|---|---|---|---|---|---|
| USUBJID | TRT01P | AVISIT | PARAM | AVAL | EGABCOM | |
| S123456-A7890-6AB001 | New drug | Baseline | QT interval | 451 | | |
| S123456-A7890-6AB001 | New drug | 5 | QT interval | 432 | | |
| S123456-A7890-6AB001 | New drug | 10 | QT interval | 438 | | |
| S123456-A7890-6AB001 | New drug | 12 | QT interval | 420 | | |
| S123456-A7890-6AB002 | Placebo | Baseline | QT interval | 425 | | |
| S123456-A7890-6AB003 | Placebo | Baseline | QT interval | 413 | | |
| S123456-A7890-6AB003 | Placebo | 5 | QT interval | 400 | | |
| S123456-A7890-6AB003 | Placebo | 10 | QT interval | 384 | | |
| S123456-A7890-6AB003 | Placebo | 12 | QT interval | 400 | | |
| S123456-A7890-6AB004 | Placebo | Baseline | QT interval | 403 | | |
| S123456-A7890-6AB004 | Placebo | 5 | QT interval | 510 | | |
| S123456-A7890-6AB004 | Placebo | 10 | QT interval | 512 | | |
| S123456-A7890-6AB004 | Placebo | 12 | QT interval | 454 | | |
| S123456-A7890-6AC001 | Placebo | Baseline | QT interval | 421 | | |
| S123456-A7890-6AC001 | Placebo | 5 | QT interval | 430 | | |
| ⋮ | ⋮ | ⋮ | ⋮ | ⋮ | ⋮ | |

(Partially extracted data)

Fig. 4

Table 14.1.1.1  Patient Disposition
All Randomized Patients

|  |  |  | Placebo N=** n (%) | S-123456 N=** n (%) |
|---|---|---|---|---|
| Treatment period | Completed |  | ** (**.*) | ** (**.*) |
|  | Withdrawn |  | ** (**.*) | ** (**.*) |
|  | Reason for withdrawal | Adverse event | ** (**.*) | ** (**.*) |
|  |  | Protocol violation | ** (**.*) | ** (**.*) |
|  |  | Lack of efficacy | ** (**.*) | ** (**.*) |
|  |  | Withdrawal by subject | ** (**.*) | ** (**.*) |
|  |  | Lost to follow-up | ** (**.*) | ** (**.*) |
|  |  | Other | ** (**.*) | ** (**.*) |
| Proceeded to taper period |  |  |  |  |
| Taper period | Completed |  | ** (**.*) | ** (**.*) |
|  | Withdrawn |  | ** (**.*) | ** (**.*) |
|  | Reason for withdrawal | Adverse event | ** (**.*) | ** (**.*) |
|  |  | Protocol violation | ** (**.*) | ** (**.*) |
|  |  | Lack of efficacy | ** (**.*) | ** (**.*) |
|  |  | Withdrawal by subject | ** (**.*) | ** (**.*) |
|  |  | Lost to follow-up | ** (**.*) | ** (**.*) |
|  |  | Other | ** (**.*) | ** (**.*) |
| Enrolled in A3133 |  |  | ** (**.*) | ** (**.*) |

For the summary in treatment period, the row of 'Proceeded to taper period' or the row of 'Enrolled in A3133', N is used as the denominator of percentage.
For the summary in taper period, the number of patients for the row of 'Proceeded to taper period' is used as the denominator of percentage.

--- Programming Note ---
> Reference: SAP Section 6.1.1
> Output File: E_SAR_A7890_TAB14_1_1_1
> "N=**" represents the number of cases assigned to each group; N is the denominator of the rate of each reason for withdrawal in taper period.
> In the "Proceeded to taper period", the number of cases proceeded to taper period is shown. This number of cases is used for the denominator of the rate of each reason for withdrawal in taper period.
> N is the denominator of the rate in the case of "Proceeded to taper period', 'Enrolled in A3133".
> The expression and the order of each reason for withdrawal follows those in database information.
> When the number of relevant cases is 0, "0" is filled in.

Fig. 9A

| PRODUCT | PROTOCOL | TYPE_TLF_CONTENTS | TLF_DISPLAY_ID | COLUMN_NO | ROW_NO | CELL_DATA | IS_GROUP | IS_CATEGORY | ALL_SINGLE_ROW_LAST_IDX |
|---|---|---|---|---|---|---|---|---|---|
| S-123456 | A7890 | Table | Table 14.1.1.1 | 0 | 0 |  | 0 | 0 | 20 |
| S-123456 | A7890 | Table | Table 14.1.1.1 | 1 | 0 |  | 0 | 0 | 20 |
| S-123456 | A7890 | Table | Table 14.1.1.1 | 2 | 0 |  | 0 | 0 | 20 |
| S-123456 | A7890 | Table | Table 14.1.1.1 | 3 | 0 | Placebo@N=**@n (%) | 1 | 0 | 20 |
| S-123456 | A7890 | Table | Table 14.1.1.1 | 4 | 0 | S-123456@N=**@n (%) | 1 | 0 | 20 |
| S-123456 | A7890 | Table | Table 14.1.1.1 | 0 | 1 | Treatment period | 0 | 1 | 20 |
| S-123456 | A7890 | Table | Table 14.1.1.1 | 1 | 1 | Completed | 0 | 1 | 20 |
| S-123456 | A7890 | Table | Table 14.1.1.1 | 2 | 1 |  | 0 | 0 | 20 |
| S-123456 | A7890 | Table | Table 14.1.1.1 | 3 | 1 | ** (**.*) | 0 | 0 | 20 |
| S-123456 | A7890 | Table | Table 14.1.1.1 | 4 | 1 | ** (**.*) | 0 | 0 | 20 |
| S-123456 | A7890 | Table | Table 14.1.1.1 | 0 | 2 |  | 0 | 0 | 20 |
| S-123456 | A7890 | Table | Table 14.1.1.1 | 1 | 2 | Withdrawn | 0 | 1 | 20 |
| S-123456 | A7890 | Table | Table 14.1.1.1 | 2 | 2 |  | 0 | 0 | 20 |
| S-123456 | A7890 | Table | Table 14.1.1.1 | 3 | 2 | ** (**.*) | 0 | 0 | 20 |
| S-123456 | A7890 | Table | Table 14.1.1.1 | 4 | 2 | ** (**.*) | 0 | 0 | 20 |
| S-123456 | A7890 | Table | Table 14.1.1.1 | 0 | 3 |  | 0 | 0 | 20 |
| S-123456 | A7890 | Table | Table 14.1.1.1 | 1 | 3 | Reason for withdrawal | 0 | 1 | 20 |
| S-123456 | A7890 | Table | Table 14.1.1.1 | 2 | 3 | Adverse event | 0 | 1 | 20 |
| S-123456 | A7890 | Table | Table 14.1.1.1 | 3 | 3 | ** (**.*) | 0 | 0 | 20 |
| S-123456 | A7890 | Table | Table 14.1.1.1 | 4 | 3 | ** (**.*) | 0 | 0 | 20 |
| S-123456 | A7890 | Table | Table 14.1.1.1 | 0 | 4 |  | 0 | 0 | 20 |
| S-123456 | A7890 | Table | Table 14.1.1.1 | 1 | 4 |  | 0 | 0 | 20 |
| S-123456 | A7890 | Table | Table 14.1.1.1 | 2 | 4 | Protocol violation | 0 | 1 | 20 |
| S-123456 | A7890 | Table | Table 14.1.1.1 | 3 | 4 | ** (**.*) | 0 | 0 | 20 |
| S-123456 | A7890 | Table | Table 14.1.1.1 | 4 | 4 | ** (**.*) | 0 | 0 | 20 |
| S-123456 | A7890 | Table | Table 14.1.1.1 | 0 | 5 |  | 0 | 0 | 20 |
| S-123456 | A7890 | Table | Table 14.1.1.1 | 1 | 5 |  | 0 | 0 | 20 |
| S-123456 | A7890 | Table | Table 14.1.1.1 | 2 | 5 | Lack of efficacy | 0 | 1 | 20 |
| S-123456 | A7890 | Table | Table 14.1.1.1 | 3 | 5 | ** (**.*) | 0 | 0 | 20 |
| S-123456 | A7890 | Table | Table 14.1.1.1 | 4 | 5 | ** (**.*) | 0 | 0 | 20 |
| S-123456 | A7890 | Table | Table 14.1.1.1 | 0 | 6 |  | 0 | 0 | 20 |
| S-123456 | A7890 | Table | Table 14.1.1.1 | 1 | 6 |  | 0 | 0 | 20 |
| S-123456 | A7890 | Table | Table 14.1.1.1 | 2 | 6 | Withdrawal by subject | 0 | 1 | 20 |
| S-123456 | A7890 | Table | Table 14.1.1.1 | 3 | 6 | ** (**.*) | 0 | 0 | 20 |
| S-123456 | A7890 | Table | Table 14.1.1.1 | 4 | 6 | ** (**.*) | 0 | 0 | 20 |
| S-123456 | A7890 | Table | Table 14.1.1.1 | 0 | 7 |  | 0 | 0 | 20 |
| S-123456 | A7890 | Table | Table 14.1.1.1 | 1 | 7 |  | 0 | 0 | 20 |
| S-123456 | A7890 | Table | Table 14.1.1.1 | 2 | 7 | Lost to follow-up | 0 | 1 | 20 |
| S-123456 | A7890 | Table | Table 14.1.1.1 | 3 | 7 | ** (**.*) | 0 | 0 | 20 |
| S-123456 | A7890 | Table | Table 14.1.1.1 | 4 | 7 | ** (**.*) | 0 | 0 | 20 |
| S-123456 | A7890 | Table | Table 14.1.1.1 | 0 | 8 |  | 0 | 0 | 20 |
| S-123456 | A7890 | Table | Table 14.1.1.1 | 1 | 8 |  | 0 | 0 | 20 |
| S-123456 | A7890 | Table | Table 14.1.1.1 | 2 | 8 | Other | 0 | 1 | 20 |
| S-123456 | A7890 | Table | Table 14.1.1.1 | 3 | 8 | ** (**.*) | 0 | 0 | 20 |
| S-123456 | A7890 | Table | Table 14.1.1.1 | 4 | 8 | ** (**.*) | 0 | 0 | 20 |
| S-123456 | A7890 | Table | Table 14.1.1.1 | 0 | 9 |  | 0 | 0 | 20 |
| S-123456 | A7890 | Table | Table 14.1.1.1 | 1 | 9 |  | 0 | 0 | 20 |
| S-123456 | A7890 | Table | Table 14.1.1.1 | 2 | 9 |  | 0 | 0 | 20 |
| S-123456 | A7890 | Table | Table 14.1.1.1 | 3 | 9 |  | 0 | 0 | 20 |
| S-123456 | A7890 | Table | Table 14.1.1.1 | 4 | 9 |  | 0 | 0 | 20 |
| S-123456 | A7890 | Table | Table 14.1.1.1 | 0 | 10 | Proceeded to taper period | 0 | 1 | 20 |
| S-123456 | A7890 | Table | Table 14.1.1.1 | 1 | 10 |  | 0 | 0 | 20 |
| S-123456 | A7890 | Table | Table 14.1.1.1 | 2 | 10 |  | 0 | 0 | 20 |

Fig. 9B

| PRODUCT | PROTOCOL | TYPE_TLF_CONTENTS | TLF_DISPLAY_ID | TITLE | FOOTNOTE | PROGRAMMING | POPULATION | COLUMNS_WIDTH | COLUMNS_ALIGN | SECTION_ORIENT |
|---|---|---|---|---|---|---|---|---|---|---|
| S-123456 | A7890 | Table | Table 14.1.1.1 | Patient Disposition | For the summary in treatment period, the row of "Proceeded to taper period or the row of "Enrolled in A3133" is used as the denominator of percentage.@For the summary in taper period, the number of patients for the row of "Proceeded to taper period is used as the denominator of percentage.@ | Reference: SAP Section 6.1.1 Output File: E_SAR_A7890_TAB14_1_1_1. "N=***" shows the denominator of cases assigned to each group. N indicates the denominator of each rate in treatment period. In the "Proceeded to taper period", the number of cases proceeded to taper period is shown. This number of cases is used for the denominator of the rate of taper period. N is the denominator of the rate of withdrawal in taper period. Enrolled in A3133". The expression and the display order of each reason for withdrawal follows those in database information. When the number of relevant cases is 0, "0" is filled in. | All Randomized Patients | 5.7cm 3.4cm 3.8cm 2.7cm 2.8cm | L L L C C | landscape |
| S-123456 | A7890 | Table | Table 14.1.1.1.1 | Patient Disposition in Treatment period by Category (Baseline Weight and Sex) | | Reference: SAP Section 6.1.1 Output File: E_SAR_A7890_TAB14_1_1_1. "N" in the "n" row shows the number of cases assigned to each category in each group. The denominator of each rate is in each category section. The expression and the display order of each reason for withdrawal follows those in database information. When the number of relevant cases is 0, "0" is filled in. | All Randomized Patients | 3.0cm 4.0cm 3.4cm 3.8cm 2.7cm 2.8cm | L L L L C C | landscape |
| S-123456 | A7890 | Table | Table 14.1.1.2 | Patient Disposition Before Randomization | | Reference: SAP Section 6.1.1 Output File: E_SAR_A7890_TAB14_1_1_2. "N=***" shows the number of enrolled cases. N indicates the denominator of each rate. The expression and the display order of each reason for withdrawal follows those in database information. When the number of relevant cases is 0, "0" is filled in. | Enrolled Patients | 6.2cm 3.9cm 4.2cm | L L C | landscape |
| S-123456 | A7890 | Table | Table 14.1.2 | Analysis Populations | [a] Fisher's exact test.@ | Reference: SAP Section 6.1.2 and 6.1.3 Output File: E_SAR_A7890_TAB14_1_2. "N=***" N indicates the denominator of each rate. The expression and the display order of each reason for exclusion follows those in database information. When the test result is not obtained, the p-value is indicated using 3 hyphens. When the number of relevant cases is 0, "0" is filled in. | All Randomized Patients | 5.9cm 1.8cm 1.9cm 1.9cm 2.3cm | L L C C C | landscape |
| S-123456 | A7890 | Table | Table 14.1.3.1 | Demographics and Baseline Characteristics for FAS | [a] Pw, Welch's t-test; Pe, Fisher's exact test.@ | Reference: SAP Section 6.1.3 Output File: E_SAR_A7890_TAB14_1_3_1. "N=***" shows the number of cases in each group in an analysis target population. N indicates the denominator of each rate. When the test result is not obtained, the " " (three half-width spaces) is output to the P-value cell. The number of digits displayed is as described in "Mock up". When the number of relevant cases is 0, "0" is filled in. | FAS | 7.7cm 6.0cm 1.9cm 1.9cm 2.3cm | L L C C C | landscape |
| S-123456 | A7890 | Table | Table 14.1.3.2 | Demographics and Baseline Characteristics for Safety Population | [a] Pw, Welch's t-test; Pe, Fisher's exact test.@ | Reference: SAP section 6.1.4 Output File: E_SAR_A7890_TAB14_1_3_2; this is prepared in the same format as in Table 14.1.3.1 while Safety Population is a target. When the number of relevant cases is 0, "0" is filled in. | Safety Population | 7.7cm 6.0cm 1.9cm 1.9cm 2.3cm | L L C C C | landscape |
| S-123456 | A7890 | Table | Table 14.1.3.3 | Previous Disease | | Reference: SAP section 6.1.4 Output File: E_SAR_A7890_TAB14_1_3_3. "N=***" shows the number of cases in each group in an analysis target population. N indicates the denominator of each rate. The disease name used is a MedDRA preferred term. The display order is according to the number of cases in the investigational drug group in a descending manner. When the number of cases is the same, the alphabetical order is used. When the | Safety Population | 6.5cm 2.1cm 2.1cm | L C C | landscape |

Fig. 10

| Condition | Detail | Pattern classification in TLF shells |||||||||||||||||||
|---|---|---|---|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 | 15.2 | 15.3 | 15.4 | 16 |
| a-1 | Table number includes "table" | Y | Y | Y | Y | Y | Y | Y | Y | Y | Y | Y | Y | Y | Y | | | | |
| a-2 | Table number includes "listing" | | | | | | | | | | | | | | | Y | Y | Y | |
| b-1 | With "adverse" | | | | | | | | Y | Y | Y | Y | Y | | | | | | |
| b-2 | Without "adverse" | Y | Y | Y | Y | Y | Y | Y | | | | | | | Y | | | | |
| c-1 | With "by" | | | | | | | | | | Y | Y | Y | | | | | | |
| c-2 | Without "by" | | | | | | | | Y | Y | | | | | | | | | |
| d-1 | With "severity", "outcome", "causality", or "onset" | | | | | | | | | | | Y | Y | | | | | | |
| d-2 | Without "severity", "outcome", "causality", or "onset" | | | | | | | | | | | | | | Y | | | | |
| e-1 | With "overall" | | | | | | | | Y | | | | | | | | | | |
| e-2 | With "incidence" | | | | | | | | | Y | | | | | | | | | |
| f-1 | The macro variable ae_type of classification_TFLs.sas is 1 (the display of categories in a summary table for each severity or others is in a portrait style) | | Y | | | | | | | | Y | | | | | | | | |
| f-2 | The macro variable ae_type of classification_TFLs.sas is 2 (the display of categories in a summary table for each severity or others is in a landscape style) | | | Y | | | | | | | | Y | | | | | | | |
| g | With "summary" | | | | | | | | | | | | | Y | | | | | |
| h | With "categorized", "urinalysis", or "electrocardiographic assessment" | | | | | | | | | | | | | | Y | | | | |
| i | With "disposition" or "withdrawal" | Y | | | | | | | | | | | | | | | | | |
| j | With "analysis population" | | Y | | | | | | | | Y | | | | | | | | |
| k | With "demographic" or "characteristics" | | | Y | | | | | | | | | Y | | | | | | |
| l | With "concomitant" | | | | Y | | | | | | | | | | | | | | |
| m | With "concurrent medical conditions", "prior therapies", "prior drugs", "previous medical conditions", "previous disease", or "concurrent disease" | | | | | Y | | | | | | | | | | | | | |
| n | With "treatment compliance" | | | | | | Y | | | | | | | | | | | | |
| o | With "exposure" | | | | | | | Y | | | | | | | | | | | |
| p | With "adverse event" or "death" | | | | | | | | | | | | | | | Y | | | |
| q | The table number includes "listing 16.2.8" and the title does not include "urinalysis" | | | | | | | | | | | | | | | | Y | | |
| r | The table number includes "listing 16.2.8" and the title includes "urinalysis" | | | | | | | | | | | | | | | | | Y | |
| s | With "fig" | | | | | | | | | | | | | | | | | | Y |

Table 14.1.1.1 Patient Disposition
All Randomized Patients

| | | | Placebo<br>N=<br>n (%) | 0.04 mg/kg<br>N=<br>n (%) | 0.08 mg/kg<br>N=<br>n (%) | 0.12 mg/kg<br>N=<br>n (%) |
|---|---|---|---|---|---|---|
| Treatment Period | Completed | | ** (**.*) | ** (**.*) | ** (**.*) | ** (**.*) |
| | Withdrawn | | ** (**.*) | ** (**.*) | ** (**.*) | ** (**.*) |
| | Reason for withdrawal | Ineligible | ** (**.*) | ** (**.*) | ** (**.*) | ** (**.*) |
| | | Lost to follow-up | ** (**.*) | ** (**.*) | ** (**.*) | ** (**.*) |
| | | Withdrawal by subject or representative | ** (**.*) | ** (**.*) | ** (**.*) | ** (**.*) |
| | | Adverse event | ** (**.*) | ** (**.*) | ** (**.*) | ** (**.*) |
| | | Lack of efficacy | ** (**.*) | ** (**.*) | ** (**.*) | ** (**.*) |
| | | Other | ** (**.*) | ** (**.*) | ** (**.*) | ** (**.*) |
| Taper Period | Completed | | ** (**.*) | ** (**.*) | ** (**.*) | ** (**.*) |
| | Withdrawn | | ** (**.*) | ** (**.*) | ** (**.*) | ** (**.*) |
| | Reason for withdrawal | Ineligible | ** (**.*) | ** (**.*) | ** (**.*) | ** (**.*) |
| | | Lost to follow-up | ** (**.*) | ** (**.*) | ** (**.*) | ** (**.*) |
| | | Withdrawal by subject or representative | ** (**.*) | ** (**.*) | ** (**.*) | ** (**.*) |
| | | Adverse event | ** (**.*) | ** (**.*) | ** (**.*) | ** (**.*) |
| | | Lack of efficacy | ** (**.*) | ** (**.*) | ** (**.*) | ** (**.*) |
| | | Other | ** (**.*) | ** (**.*) | ** (**.*) | ** (**.*) |

-- Programming Note --
> Reference: SAP Section 6.1.1
> Output File: E_SAR_A3122_TAB14_1_1_1
> "N=**" shows the number of cases assigned to each group. N indicates the denominator of each rate.
> Each reason for withdrawal is expressed according to database information (2)

Table 14.1.1.2 Withdrawal in Treatment Period by Duration of Treatment
All Randomized Patients

| Period (week) [a] | Reason for Withdrawal | Placebo<br>N=<br>n (%) | 0.04 mg/kg<br>N=<br>n (%) | 0.08 mg/kg<br>N=<br>n (%) | 0.12 mg/kg<br>N=<br>n (%) |
|---|---|---|---|---|---|
| <1 | Ineligible | ** (**.*) | ** (**.*) | ** (**.*) | ** (**.*) |
| | Lost to follow up | ** (**.*) | ** (**.*) | ** (**.*) | ** (**.*) |
| | Withdrawal by subject or representative | ** (**.*) | ** (**.*) | ** (**.*) | ** (**.*) |
| | Adverse event | ** (**.*) | ** (**.*) | ** (**.*) | ** (**.*) |
| | Lack of efficacy | ** (**.*) | ** (**.*) | ** (**.*) | ** (**.*) |
| | Other | ** (**.*) | ** (**.*) | ** (**.*) | ** (**.*) |
| >=1 to <2 | Ineligible | ** (**.*) | ** (**.*) | | |
| | : | : | : | ** (**.*) | ** (**.*) |
| >=2 to <3 | Ineligible | ** (**.*) | ** (**.*) | | |
| | : | : | : | ** (**.*) | ** (**.*) |
| >=3 to <4 | Ineligible | ** (**.*) | ** (**.*) | | |
| | : | : | : | ** (**.*) | ** (**.*) |
| >=4 to <5 | Ineligible | ** (**.*) | ** (**.*) | ** (**.*) | ** (**.*) |
| | : | : | : | : | : |
| >=5 to <7 | Ineligible | ** (**.*) | ** (**.*) | ** (**.*) | ** (**.*) |
| | : | : | : | : | : |

[a] Based on allowance of visit.

-- Programming Note --
> Reference: SAP Section 6.1.1
> Output File: E_SAR_A3122_TAB14_1_1_2
> "N=**" shows the number of cases assigned to each group. N indicates the denominator of each rate.
> Each reason for withdrawal is expressed according to database information
> In consideration of the allowed range of each visit and the date of visit when the case is withdrawn, which period is applicable is determined. The allowed width of testing period is determined with reference to PC.
> Data when the treatment period is ended is a subject matter.

| Order | Dataset | Description | Class | Structure | Purpose |
|---|---|---|---|---|---|
| 1 | ADSL | Subject-Level Analysis | SUBJECT LEVEL ANALYSIS DATASET | one record per subject | Analysis |
| 2 | ADAE | Adverse Event Analysis Dataset | ADAM OTHER | One record per subject per each AE recorded in SDTM AE domain | Analysis |
| 3 | ADEG | Electrocardiogram Analysis Dataset | BASIC DATA STRUCTURE | One record per subject per parameter per analysis visit per analysis date | Analysis |

(2)

| Dataset | Order | Key Sequend | Variable | Label | Vartype | Length | Format | Codelist | Origin |
|---|---|---|---|---|---|---|---|---|---|
| ADSL | 1 | 1 | STUDYID | Study Identifier | Char | 40 | | | Predecessor |
| ADSL | 2 | 2 | USUBJID | Unique Subject Identifier | Char | 40 | | | Predecessor |
| ADSL | 3 | 3 | SUBJID | Subject Identifier for the Study | Char | 40 | | | Predecessor |
| ADSL | 4 | | SITEID | Study Site Identifier | Char | 40 | | | Derived |
| ADSL | 5 | | SITEGR1 | Pooled Site Group 1 | Char | 200 | | SITEGR1 | Derived |
| ADSL | 6 | | SITEGR1N | Pooled Site Group 1 (N) | Num | 8 | | SITEGR1 | Assigned |
| ADSL | 7 | | REGION1 | Geographic Region 1 | Char | 200 | | REGION1 | Derived |

(3)

| ID | Name | Company Terminology Code | NCI Codelist Code | Data Type | Order | Term | Raw Term | NCI Term Code | Decoded Value |
|---|---|---|---|---|---|---|---|---|---|
| AGEU | Age Unit | | C66781 | text | 1 | YEARS | | C29848 | Years |
| ARM | Description of Planned Arm | | | text | 1 | S-XXXXXX 10 mg | | | |
| ARM | Description of Planned Arm | | | text | 2 | S-XXXXXX 20 mg | | | |
| ARM | Description of Planned Arm | | | text | 3 | S-XXXXXX 40 mg | | | |
| ARM | Description of Planned Arm | | | text | 4 | Placebo | | | |
| RACE | Race | S_RACE | C74457 | text | 1 | AMERICAN INDIAN OR ALASKA NATIVE | American Indian or Alaska Native | C41259 | |
| RACE | Race | S_RACE | C74457 | text | 2 | ASIAN | Asian | C41260 | |
| RACE | Race | S_RACE | C74457 | text | 3 | BLACK OR AFRICAN AMERICAN | Black or African American | C16352 | |

| Item No. | Display Identifier | Display Name | Population | Dataset | Selection Criteria | Analysis Variable |
|---|---|---|---|---|---|---|
| 1 | Table 14.1.1.1 | Patient Disposition | All Randomized Patients | ADDS | DSDECODC in ('002') | DSDECODC |
| 2 | Table 14.1.1.2 | Period of Withdrawal | All Randomized Patients | ADDS | DSDECODC in ('002') | DSDECODC |
| 3 | Table 14.1.1.3 | Patient Disposition Before Randomization | Enrolled Patients | ADDS | DSDECODC in ('001') | DSDECODC |
| 4 | Table 14.1.1.4 | Patient Disposition in Follow-up Period | All Randomized Patients | ADDS | DSDECODC in ('002') | DSDECODC |
| 5 | Table 14.1.2 | Analysis Populations | All Randomized Patients | ADDS ADSL | [ADDS] DSDECODC in ('002') | [ADSL] SAFEFL, SAFECLAC, FASFL, PPROTFL, SUBJCLAC |
| 6 | Table 14.1.3 | Demographic Characteristics | FAS | ADSL | FASFL in ('Y') | SEXC, AGE, RACEC, ETHNICC, MHYNC, CHYNC, PRDRYNC, HEIGHT, WEIGHT |
| 7 | Table 14.1.4 | Previous Medical Conditions | FAS | ADMH | FASFL in ('Y') | MHDECOD |
| 8 | Table 14.1.5 | Prior Drugs | FAS | ADCD | FASFL in ('Y') and CMENRTPT in ('BEFORE') | CMDECOD |
| 9 | Table 14.1.6 | Prior Therapies | FAS | ADCT | FASFL in ('Y') and CMENRTPT in ('BEFORE') | CMTRT |

(2)

| Item No. | TLF Number | Title | Population | Language | Sub Title | Footnote 1 | Footnote 2 | Footnote 3 | Footnote 4 | Footnote 5 | Footnote 6 | Footnote 7 | Footnote 8 | Footnote 9 |
|---|---|---|---|---|---|---|---|---|---|---|---|---|---|---|
| 1 | Table 14.1.1.1 | Patient Disposition | All Randomized Patients | E | | | | | | | | Common footnote #1 | Common footnote #2 | Common footnote #3 |
| 2 | Table 14.1.1.2 | Period of Withdrawal | All Randomized Patients | E | | | | | | | | Common footnote #1 | Common footnote #2 | Common footnote #3 |
| 3 | Table 14.1.1.3 | Patient Disposition Before Randomization | Enrolled Patients | E | | | | | | | | Common footnote #1 | Common footnote #2 | Common footnote #3 |
| 4 | Table 14.1.1.4 | Patient Disposition in Follow-up Period | All Randomized Patients | E | | | | | | | | Common footnote #1 | Common footnote #2 | Common footnote #3 |
| 5 | Table 14.1.2 | Analysis Populations | All Randomized Patients | E | | | | | | | | Common footnote #1 | Common footnote #2 | Common footnote #3 |
| 6 | Table 14.1.3 | Demographic Characteristics | FAS | E | | | | | | | | Common footnote #1 | Common footnote #2 | Common footnote #3 |
| 7 | Table 14.1.4 | Previous Medical Conditions | FAS | E | | | | | | | | Common footnote #1 | Common footnote #2 | Common footnote #3 |
| 8 | Table 14.1.5 | Prior Drugs | FAS | E | | | | | | | | Common footnote #1 | Common footnote #2 | Common footnote #3 |
| 9 | Table 14.1.6 | Prior Therapies | FAS | E | | | | | | | | Common footnote #1 | Common footnote #2 | Common footnote #3 |

Fig. 15

| Item No. | Display Identifier | Display Name | Population | Dataset | Analysis Variable | Pattern_m | Pattern_y | P_Dataset | P_Analysis Variable |
|---|---|---|---|---|---|---|---|---|---|
| 1 | Table 14.1.1.1 | Patient Disposition | All Enrolled Patients | | | 1 | 1 | ADSL ADDS | ADDS.DSDECODC, ADDS.DSDOSEOC, ADDS.EPOCHC, ADDS.TRTAC, ADDS.TRTPC, ADSL.COMPLFL, ADSL.RACEC, ADSL.TCOMPLFL, ADSL.TRT01AC, ADSL.TRT01PC |
| 2 | Table 14.1.1.2 | Patient Disposition in Screening Period for New Patients | New Patients Enrolled in Screening Period | | | 1 | 1 | ADCD ADCT ADSL ADDS | ADCD.CDCOM, ADCD.CMR1AEPE, ADCD.CMR2AEPE, ADCD.CMR3AEPE, ADCD.CMR4AEPE, ADCD.CMR5AEPE, ADCD.CMROUTEC, ADCD.TRTAC, ADCD.TRTPC, ADCT.CMR1AEPE, ADCT.CMR2AEPE, ADCT.CMR3AEPE, ADCT.CMR4AEPE, ADCT.CMR5AEPE, ADCT.TRTAC, ADCT.TRTPC, ADDS.DSDECODC, ADDS.TRTAC, ADDS.TRTPC, ADSL.RACEC, ADSL.TRT01AC, ADSL.TRT01PC |
| 3 | Table 14.1.2 | Analysis Populations | All Enrolled Patients | | | 2 | 1 | ADSL | ADSL.SAFECLAC, ADSL.SAFFL, ADSL.SUBJCLAC, ADSL.TRT01AC, ADSL.TRT01PC |
| 4 | Table 14.1.3.1 | Demographics and Baseline Characteristics for FAS | FAS | | | 3 | 3 | ADSL | ADSL.AGE, ADSL.AGEC, ADSL.BADHDC, ADSL.CHYNC, ADSL.CODRYNC, ADSL.CDTHYNC, ADSL.DIAG, ADSL.DIAGC, ADSL.ETHNIC, ADSL.ETHNICC, ADSL.HEIGHT, ADSL.MHYNC, ADSL.PRDRYN, ADSL.PRDRYNC, ADSL.PRTHYN, ADSL.PRTHYNC, ADSL.RACE, ADSL.RACEC, ADSL.SEX, ADSL.SEXC, ADSL.TRT01AC, ADSL.TRT01PC, ADSL.WEIGHT, ADSL.WEIGHTC1, ADSL.WEIGHTC2 |

| Item No. | Display Identifier | Display Name | Population | Dataset | Analysis Variable | Pattern_t | Pattern_m | Pattern_v |
|---|---|---|---|---|---|---|---|---|
| 1 | Table 14.1.1.1 | Patient Disposition | All Enrolled Patients | ADSL ADDS | [ADDS] DSDECODC | | 1 | 1 |
| 2 | Table 14.1.1.2 | Patient Disposition in Screening Period for New Patients | New Patients Enrolled in Screening Period | ADSL ADDS | [ADDS] DSDECODC | | | |
| 3 | Table 14.1.2 | Analysis Populations | All Enrolled Patients | ADSL | FASFL, SAFFL, SUBJCLAC, SAFECLAC | | 2 | |
| 4 | Table 14.1.3.1 | Demographics and Baseline Characteristics for FAS | FAS | ADSL | SEXC, AGEC, AGE, HEIGHT, WEIGHTC1, WEIGHT, RACEC, ETHNICC, MHYNC, CHYNC, PRDRYNC, PRTHYNC, DIAGC, BADHDC, BADHD | | 3 | 3 |

| Dataset | Variable | LABEL |
|---|---|---|
| ADSL | COMPLFL | Completed |
| ADSL | COMPLFL | Withdrawn |
| ADDS | DSDECODC | Reson for withdrawn |
| ADSL | TCOMPLFL | Completed |
| ADSL | TCOMPLFL | Withdrawn |
| ADDS | DSDECODC | Reason for withdrawn |
| ADSL | TRI01PC | S-877503 N=** n (%) |
| ADSL | TRI01PC | Placebo N=** n (%) |
| ADSL | SAFEL | Subjects included in safety population |
| ADSL | SAFEL | Subjects excluded from safety population |
| ADSL | SAFECLAC | Reason for exclusion |
| ADSL | TRT01PC | S-877503 N=** n (%) |
| ADSL | TRT01PC | Placebo N=** n (%) |
| ADSL | SEXC | Sex |
| ADSL | AGE | Age (years) |
| ADSL | HEIGHT | Height (cm) |
| ADSL | WEIGHT | Weight (kg) |
| ADSL | BMI | BMI (kg/m2) |
| ADSL | RACEC | Race |
| ADSL | ETHICC | Ethinicity |
| ADSL | BLDHYNC | Blood donation history |
| ADSL | PRTHYNC | Prior therapy |
| ADSL | PRDRYNC | Prior drug |
| ADSL | HAODYNC | Drinking habit |
| ADSL | HAOSYNC | Smoking habit |

Fig. 22

| Protocol | PRODUCT | PROTOCOLID | Table | Table2 | TITLE | T_OVARS | T_HEADER | T_LENGTH |
|---|---|---|---|---|---|---|---|---|
| s-123456A7890 | s123456 | a7890 | Figure.14.2.1 | Figure 14.2.1 | LS Mean and SE in Changes from Baseline for: ADHD RS-IV with Adult Prompts Total Score by Time Point | COL1 COL2 COL3 COL4 COL5 COL6 COL7 COL8 | | |
| s-123456A7890 | s123456 | a7890 | Listing.16.2.1.1 | Listing 16.2.1.1 | Withdrawals in Screening Period | COL1 COL2 COL3 COL4 COL5 COL6 COL7 COL8 COL9 COL10 COL11 COL12 COL13 COL14 COL15 COL16 COL17 | | 1.7cm 2.4cm 2.7cm 2.3cm 2.4cm 2.8cm |
| s-123456A7890 | s123456 | a7890 | Listing.16.2.1.2 | Listing 16.2.1.2 | Withdrawals in Treatment Period | COL1 COL2 COL3 COL4 COL5 COL6 COL7 COL8 COL9 COL10 COL11 COL12 COL13 COL14 COL15 COL16 COL17 | | 1.8cm 2.7cm 2.1cm 1.8cm 2cm 2.2cm 2.3cm 2cm 2cm 2.5cm 1.7cm |
| s-123456A7890 | s123456 | a7890 | Listing.16.2.1.3 | Listing 16.2.1.3 | Withdrawals in Taper Period | COL1 COL2 COL3 COL4 COL5 COL6 COL7 COL8 COL9 COL10 COL11 COL12 COL13 COL14 COL15 COL16 COL17 | | 1.8cm 2.7cm 2.1cm 1.8cm 2cm 2.2cm 2.3cm 2cm 2cm 2.5cm 1.7cm |
| s-123456A7890 | s123456 | a7890 | Listing.16.2.3.1 | Listing 16.2.3.1 | Patients Excluded from the Analysis Population | COL1 COL2 COL3 COL4 COL5 COL6 COL7 | | 1.6cm 1.9cm 1.3cm 2.2cm 1.7cm 1.6cm 1.5cm 6.3cm |
| s-123456A7890 | s123456 | a7890 | Listing.16.2.4.1 | Listing 16.2.4.1 | Demographic and Baseline Characteristics | COL1 COL2 COL3 COL4 COL5 COL6 COL7 COL8 COL9 COL10 COL11 COL12 COL13 | | 2.1cm 2.2cm 2.3cm 2.3cm 2.3cm 3.4cm 3.3cm 1cm 1.2cm |
| s-123456A7890 | s123456 | a7890 | Listing.16.2.4.2 | Listing 16.2.4.2 | Prior Drugs | COL1 COL2 COL3 COL4 COL5 COL6 COL7 COL8 COL9 COL11q | | 2cm 2.4cm 2.3cm 2.5cm 4cm 2.5cm 3cm |
| s-123456A7890 | s123456 | a7890 | Listing.16.2.4.3 | Listing 16.2.4.3 | Concomitant Drugs | COL1 COL2 COL3 COL4 COL5 COL6 COL7 COL8 COL9 COL10 | Reason for Use COL11 COL15 | 2cm 2.4cm 2.3cm 2.3cm 2.3cm 1.5cm 0.11cm 2.3cm 2.3cm 1.7cm |
| s-123456A7890 | s123456 | a7890 | Listing.16.2.4.4 | Listing 16.2.4.4 | Prior/Concomitant Therapies | COL1 COL2 COL3 COL4 COL5 COL6 COL7 COL8 COL9 COL10 | Reason for Use COL11 COL12 | 2cm 2.4cm 2.3cm 2.3cm 2.3cm 3.5cm 1.7cm 0.6cm 1.7cm 2.3cm 2.3cm 1.3cm |
| s-123456A7890 | s123456 | a7890 | Listing.16.2.4.5 | Listing 16.2.4.5 | Medical History | COL1 COL2 COL3 COL4 COL5 COL6 COL7 | | 2cm 2.3cm 2.3cm 2.2cm 1.3cm 4.5cm 4.5cm |
| s-123456A7890 | s123456 | a7890 | Listing.16.2.5 | Listing 16.2.5 | Treatment Compliance | COL1 COL2 COL3 COL4 COL5 COL6 COL7 COL8 | | 2.2cm 2.3cm 2.4cm 2.6cm 3.3cm 3.8cm |
| s-123456A7890 | s123456 | a7890 | Table.14.1.1.1 | Table 14.1.1.1 | Patient Disposition | COL1-COL5 | | 5.7cm 3.5cm 3.9cm 2.8cm 2.8cm |
| s-123456A7890 | s123456 | a7890 | Table.14.1.1.1.1 | Table 14.1.1.1.1 | Patient Disposition in Treatment period by C | COL1-COL6 | | 3.1cm 4.1cm 3.5cm 3.9cm 2.8cm 2.8cm |
| s-123456A7890 | s123456 | a7890 | Table.14.1.1.2 | Table 14.1.1.2 | Patient Disposition Before Randomization | COL1-COL3 | | 6.2cm 4cm 4.2cm |
| s-123456A7890 | s123456 | a7890 | Table.14.1.2 | Table 14.1.2 | Analysis Populations | COL1-COL5 | | 5.9cm 6.8cm 1.9cm 1.9cm 2.1cm |
| s-123456A7890 | s123456 | a7890 | Table.14.1.3.1 | Table 14.1.3.1 | Demographics and Baseline Characteristics | COL1-COL5 | | 7.8cm 6cm 1.9cm 1.9cm 2cm |

Fig. 23

```
/*------------------------------------------------------------*  ;
    PRODUCT ID        : @PRODUCT@
    PROTOCOL ID       : @PROTOCOLID@
    TITLE             : @Title@
    PROGRAM NAME      : @PROTOCOLID@_@program_name@_@ID_num@.sas
    ------------------------------------------------------------
    AUTHOR            : @AUTHOR@
    COMPLETION DATE   : &date.
    ------------------------------------------------------------
    MODIFIED 01       :
    CHANGES           :
    ------------------------------------------------------------
    SAS VERSION       : 9.4(DBCS)
    ------------------------------------------------------------
    DATA              :
    ------------------------------------------------------------
    NOTE              :
*------------------------------------------------------------*/
    ;
    %let studypath= Q:¥SDD¥project¥@PRODUCT@¥@PROTOCOLID@;
    %inc    &studypath.¥production¥analysis¥programs¥pc_macros¥init_def.sas ;
    %init_def(SHQ);
    %include    &tprg_v.¥fmt.sas ;

options orientation = landscape;

*================== Read ADaM ;
    proc sort data = adam.ADDS out = _adds ;
      by USUBJID ;
      where @SC_adds@ ;
    run ;

*================== Work Format ;
    proc format;
      value _wk_fmt 1 =    Completed
                    2 =    Withdrawn;
```

PROGRAM GENERATION ASSISTING SYSTEM FOR ASSISTING GENERATION OF PROGRAM FOR ANALYZING CLINICAL TRIAL

TECHNICAL FIELD

The present disclosure relates to a program generation assisting system for assisting generation of a program for analyzing a clinical trial during pharmaceutical development.

BACKGROUND ART

In pharmaceutical development, several data sets and materials are prepared by analysis work in each clinical trial. These data sets and materials are submitted at the time of application to the pharmaceutical authorities (PMDA/FDA/EMA), and are created by analyzing clinical data collected from medical institutions such as hospitals.

Pharmaceutical companies perform various types of programming to prepare data sets and materials. Examples include programming for analyzing clinical data to create a prescribed data set and programming for creating, from the prescribed data set, another data set. In addition, the pharmaceutical companies also perform programming for preparing analysis materials from other data sets.

The format of each data set is partially or entirely standardized within the pharmaceutical industry. Thus, as long as the format is standardized, programming may be generally automated. On the other hand, the format of each analysis material is not standardized, and programming with the analysis material has not been automated. Only restriction is that the analysis material should correctly reflect the analysis results. Therefore, each pharmaceutical company as well as each programmer in the pharmaceutical company has great discretion about the format of the analysis material.

Clinical data obtained in one clinical trial may be used to conduct numerous analyses, for example, 100 or more analyses. There is a room for improvement in operation efficiency in the current situation where individual programmers perform programming for preparing analysis materials at their discretion for each analysis.

The purpose of the present disclosure is to assist automation of programming for automatic generation of an analysis material prepared by analysis work in a clinical trial during pharmaceutical development.

SUMMARY OF THE INVENTION

A first program generation assisting system for assisting generation of a program for analyzing a clinical trial according to an exemplary embodiment of the present invention includes: an interface device configured to acquire text data and image data created from an image/table analysis plan that specifies a method of analyzing a clinical trial and an output format of an analysis result; and a storage device configured to store the text data and the image data; and a processing circuit configured to execute each of a first candidate prediction method using the text data and a second candidate prediction method using the image data to classify the image/table analysis plan into at least one pattern among a plurality of predetermined patterns, and then to output a result as a classification candidate.

In such a first program generation assisting system, the plurality of patterns are classified in advance according to the clinical trial analyzing method and the analysis result output format. The first program generation assisting system is provided in advance with a determination rule that defines a relationship of how each of a plurality of text strings corresponds to a pattern in which each text string is classified. Also, provided is a trained artificial neural network constructed by training with, as labeled training data, image data of each image/table analysis plan from a plurality of past clinical trials and ground truth patterns obtained by classifying the image data of each image/table analysis plan. The processing circuit uses the text strings included in the text data of the image/table analysis plan and the determination rule to output data indicating the first pattern among the plurality of patterns by executing the first candidate prediction method. Similarly, the processing circuit inputs the image data of the image/table analysis plan into the artificial neural network to acquire data indicating the second pattern output from the artificial neural network by executing the second candidate prediction method. Further, the processing circuit outputs the first pattern and the second pattern as classification candidates for the analysis material.

A second program generation assisting system for assisting generation of a program for analyzing a clinical trial according to another exemplary embodiment of the present invention includes: a storage device configured to store a database; an interface device configured to acquire data about an image/table analysis plan that specifies a method of analyzing a clinical trial and an output format of an analysis result; and a processing circuit configure to output, as a candidate, a name of at least one model data to be used for analyzing the clinical trial with reference to the database and the data about the image/table analysis plan.

The image/table analysis plan includes one or more forms, and each form specifies analysis content for each type of analysis of the clinical trial. The database stores each form of analysis materials in past clinical trials and a name of model data used in each form, namely a name of model data that is a collection of a data set and metadata for analysis. The processing circuit uses a given similarity evaluation function to calculate, for each form of the image/table analysis plan obtained, a similarity between description in the form and description in each form of analysis materials in past clinical trials. Further, the calculated similarity is used to extract a name of at least one piece of model data used in the form of analysis materials in past clinical trials, which name corresponds to the former description in the form, and then output the extracted model data name.

An analysis program generation system for generating a program for analyzing a clinical trial according to still another exemplary embodiment of the present invention includes an interface device, a storage device, and a processing circuit.

The interface device is configured to acquire the first pattern and the second pattern output from the first program generation assisting system, and acquire the name and the variable of the model data output from the second program generation assisting system. It is possible to acquire correction data for correcting the first pattern, the second pattern, the name, and/or the variable. The storage device is configured to store a template program corresponding to each of the plurality of patterns and capable of specifying the method of analyzing the clinical trial and the output format of the analysis result. When the correction data is acquired, the processing circuit creates metadata including pattern-specifying data that specifies one of the plurality of patterns, based on the corrected first pattern, second pattern, name and/or variable and the text data. In addition, when the correction data is not acquired, the processing circuit creates metadata including pattern-specifying data that specifies one of the plurality of patterns, based on the acquired first pattern, second pattern, name and/or variable and the text data. Further, the processing circuit reads a template program corresponding to each pattern specified by the pattern-specifying data, and uses the metadata to generate an analysis program from the template program.

An embodiment of the present invention makes it possible to assist automation of programming for automatic generation of an analysis material prepared by analysis work in a clinical trial during pharmaceutical development, and further to automatically generate a program for preparing an analysis material.

BRIEF DESCRIPTION OF THE DRAWINGS

FIG. 3 is a specific example of an ADaM data set.

FIG. 4 is an example of part of an image/table analysis plan, which is an image/table plan.

FIG. 9A is an example of format information among format information and layout information, which are text data extracted from the image/table analysis plan.

FIG. 9B is an example of layout information among format information and layout information, which are text data extracted from the image/table analysis plan.

FIG. 10 is an example of determination rules for rule-based prediction.

FIGS. 11(1) and 11(2) are examples of CNN input data.

FIG. 13 is examples of an ADaM data set specification (ADaM specification), which is a model specification.

FIG. 14 is examples of a form preparation-related specification (TFL specification).

FIG. 15 is an example of a form preparation-related specification before correction input.

FIG. 16 is an example of a form preparation-related specification after correction input.

FIG. 19 is an example of ADaM/variable association information.

FIG. 22 is an example of metadata for automatic generation.

FIG. 23 is an example of a template program for analysis.

DETAILED DESCRIPTION OF THE INVENTION

Figure 1:
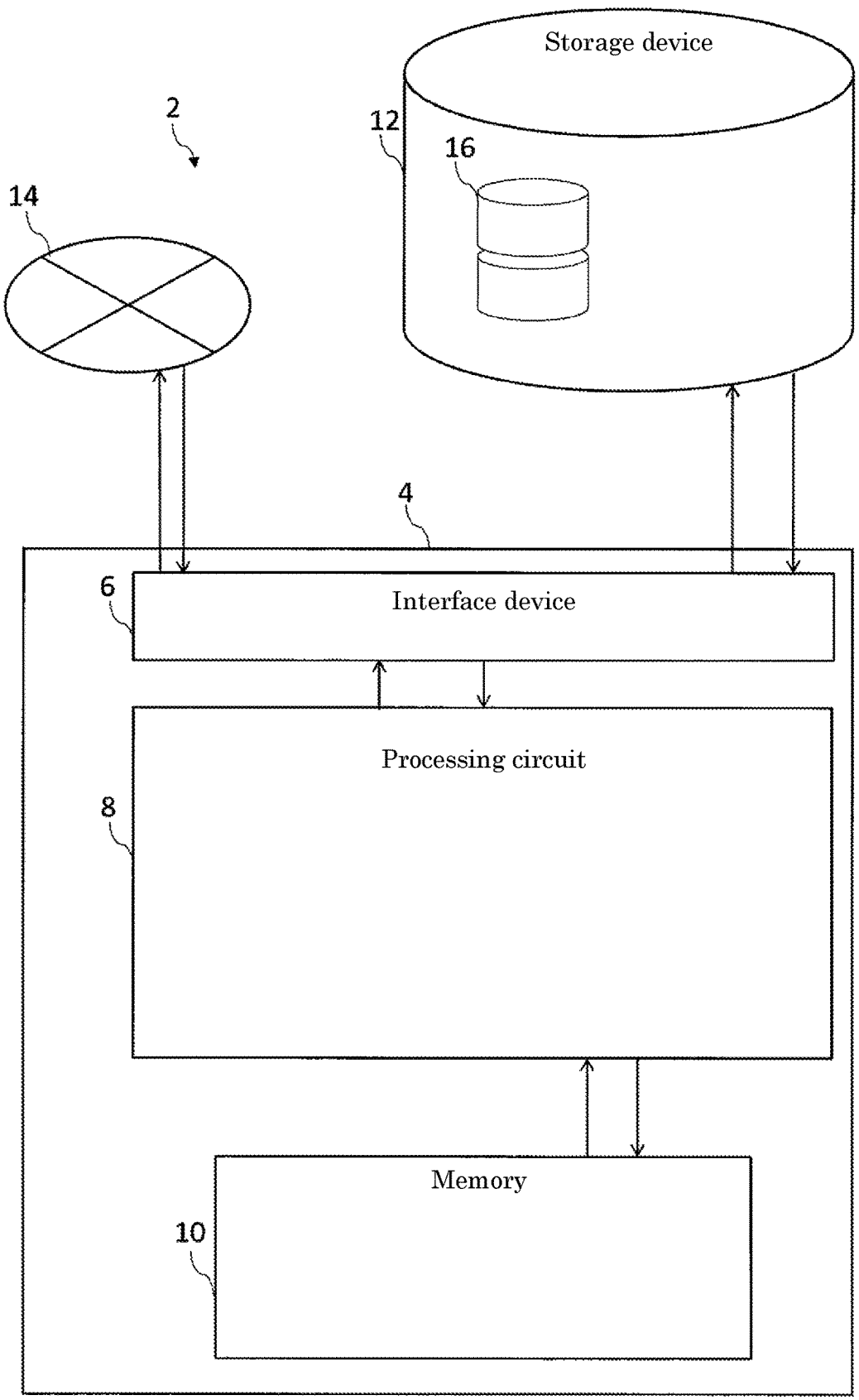
FIG. 1 is a system configuration diagram of a system of automatically generating a program for preparing an analysis material according to an embodiment.

Hereinafter, embodiments will be described in detail with reference to the drawings, if appropriate. However, unnecessarily detailed description may be omitted. For example, detailed description of a well-known matter and repeated description of substantially the same configuration may be omitted. This is to avoid unnecessary redundancy of the following description and to facilitate understanding of those skilled in the art.

Note that the present inventors provide the accompanying drawings and the following description in order for those skilled in the art to fully understand the present disclosure. Thus, they are not intended to limit the claimed subject matter.

In pharmaceutical development, several data sets and materials are prepared by analysis work in each clinical trial. These data sets and materials are submitted at the time of application to the pharmaceutical authorities (PMDA/FDA/EMA), and are created by analyzing clinical data collected from medical institutions such as hospitals.

These data sets and materials include:
(1) EDC (Electric Data Capture; Electronic Clinical Test Information Collection) raw data;
(2) SDTM (Study Data Tabulation Model)-related data set;
(3) ADaM (Analysis Data Model)-related data set;
(4) analysis materials; and
others.

Among them, SDTM is a standard model for a clinical trial data set to be submitted at the time of application to the authorities (PMDA/FDA/EMA). ADAM is an analysis data model for the clinical trial data set to be submitted at the time of application to the authorities (PMDA/FDA/EMA). FIG. 3 is a table illustrating a specific example (part) of an ADaM data set.

Pharmaceutical companies perform various types of programming for preparing these data sets and materials. Examples of the programming include programming for creating an SDTM from EDC Raw data or programming for creating an ADaM from the SDTM. Further, programming for preparing an analysis material from the ADaM is also performed. The analysis material is used for preparing, for instance, an attached document to be submitted when pharmaceutical approval review is requested.

The SDTM-related data set is standardized by a global standard development organization, and further, there is a guidance document for preparation. Accordingly, programming for preparing the data set fits automatic generation. Part of the ADaM-related data set is standardized by a global standard development organization, and there is also a guidance document for preparation. Regarding the ADaM-related data set, programming for preparing the data set can also be said to partially fit automatic generation.

Here, the data set can be prepared relatively freely by an analyst, provided that the correctness of the results of analyzing the analysis material is ensured. Here, there is a guidance document about the content itself (e.g., efficacy, safety) of the analysis material required by the authorities. However, there is neither a guidance document about its format nor standardization. For this reason, it is considered that programming for preparing an analysis material is not compatible with automation. As a result, there is no precedent of automation in practice.

It has been difficult to automate programming for automatic generation of an analysis material. This is because the following circumstances exist in a complex manner.

(1) The format of the analysis material is not standardized. So, the program for the analysis material can be created more freely than a program for preparing an SDTM and/or ADaM-related data set, and uniform algorithmization is difficult.

(2) Before preparing the analysis material, it is necessary to prepare one or more image/table analysis plans. Unfortunately, it has been difficult to extract information necessary for generating a program from these image/table analysis plans. This is because different application software used to create image/table analysis plans may have different file formats. In addition, the data format (e.g., the description position, the description content, the expression, the position of line feed code, and the numerical value of each data in the file) is structured substantially freely. Thus, in order to automatically extract the data, it has been difficult to beforehand specify, for instance, the position and the size of the data to be read. Note that the image/table analysis plan is a specification in which an analyst specifies a method of analyzing a clinical trial and an output format of an analysis result.

(3) The ADaM-related data set used for analysis and the data used for prediction of variables are mostly text data. In order to recognize the content of the text data while using a computer and prepare an analysis material, an advanced text analysis technology is required. Further, it is necessary to take into account association between pieces of text information including words and others. However, there is no electronic dictionary indicating association between pieces of text information specialized for clinical trials. It is thus difficult to acquire and implement text analysis techniques and prediction algorithms.

The present disclosure makes it possible to overcome these problems and to provide a program generation assisting system for assisting automation of programming for automatic generation of an analysis material prepared by analysis work in a clinical trial during pharmaceutical development. Further, the present disclosure provides an analysis program generation system that automatically generates a program for preparing an analysis material.

Hereinafter, preferred embodiments of the present disclosure will be described with reference to the accompanying drawings.

A system of automatically generating a program for preparing an analysis material according to an embodiment is a system for assisting automation of programming for automatic generation of an analysis material prepared by analysis work in a clinical trial during pharmaceutical development so as to automatically generate a program for preparing an analysis material. FIG. 1 is a system configuration diagram of a system 2 of automatically generating a program for preparing an analysis material according to an embodiment of the present invention. Hereinafter, the "system 2 of automatically generating a program for preparing an analysis material" is abbreviated as "system 2".

The system 2 includes a computer device 4 and a storage device 12. The computer device 4 and the storage device 12 are connected by a wired or wireless communication line, and can transmit and receive data to and from each other. The system 2 may be further connected to an external network 14, and data may be exchanged with another computer system connected to the external network 14.

The computer device 4 is, for example, a PC, a tablet computer, or a workstation computer equipped with one or more processors.

The storage device 12 is a storage device (e.g., a disk drive, a flash memory) provided outside the computer device 4, and stores various databases 16, various data sets, and various computer programs used for the computer device 4.

The various databases 16 store, for example, data acquired by the computer device 4 via the interface device 6 of the computer device 4 and various data created by the system 2, which will be described later.

The external network 14 is, for example, the Internet, and is connected to the computer device 4 via the interface device 6 such as a network terminal.

The computer device 4 further includes the interface device 6, a processing circuit 8, and a memory 10.

The interface device 6 is an interface unit capable of acquiring data from the outside, including, for example, a network terminal, a video input terminal, a USB terminal, a keyboard, and/or a mouse. Various data is acquired from the outside via the interface device 6. The data is, for example, image/table analysis plan data of a target clinical trial and image/table analysis plan data of past clinical trials, which will be described later. Other examples of the data include form preparation-related specifications (TFL specifications) and/or model specifications, namely ADaM data set specifications (ADaM specifications), in accumulated past clinical trials. After acquisition, these data may be stored in the storage device 12. Data stored in the storage device 12 may be acquired, if appropriate, in the computer device 4 via the interface device 6.

Further, various data created by the system 2 is stored, if appropriate, in the storage device 12. The various data is, for example, text data (format information and layout information) prepared from an image/table analysis plan, which will be described later. Other examples of the various data include image data of the image/table analysis plan, a table indicating how a form and description of the form correspond to model data (ADaM data), extracted "ADaM specification information", and/or model data/variable association information (ADaM/variable association information). Various data created by such a system 2 and stored, if appropriate, in the storage device 12 may be re-acquired in the computer device 4 via the interface device 6.

The processing circuit 8 includes a processor. Here, the processor includes a central processing unit (CPU) and/or a graphics processing unit (GPU). Various functions of the system 2 according to this embodiment are implemented while the processing circuit 8 executes various programs. Note that the various functions may be implemented by, for instance, an application specific integrated circuit (ASIC), or may be implemented by a combination therewith.

The processing circuit 8 in the present disclosure may include a plurality of signal processing circuits. Here, each signal processing circuit includes a central processing unit (CPU) and/or a graphics processing unit (GPU), and may be called a "processor". A certain processor may execute part of various processes in the system 2 according to this embodiment, and another processor may execute another part of the processes. For example, "micro rule-based prediction" and "macro CNN-based prediction" to be described later may be performed by different processors. That is, for example, a certain CPU may execute the "micro rule-based prediction" and a certain GPU may execute the "macro CNN-based prediction". Note that the term "CNN" means a convolutional neural network. The term is herein abbreviated as "CNN".

The memory 10 is a data rewritable storage unit inside the computer device 4, and includes, for example, a random access memory (RAM) including a large number of semiconductor storage elements. The memory 10 temporarily stores, for instance, specific computer programs, variables, and/or parameter values used when the processing circuit 8 executes various processes. Note that the memory 10 may include what is called a read only memory (ROM). The ROM pre-stores a computer program for implementing processing of the system 2 described below. The processing circuit 8 reads the computer program from the ROM and deploys the computer program in the RAM, so that the processing circuit 8 can execute the computer program.

The system 2 according to the present disclosure is constructed using a computer language such as Python or the SAS language of the SAS institute in the US. The computer language that can be used for constructing the system of automatically generating a program for preparing an analysis material according to the present disclosure is not limited thereto, and of course, other computer languages may be used.

Figure 2:
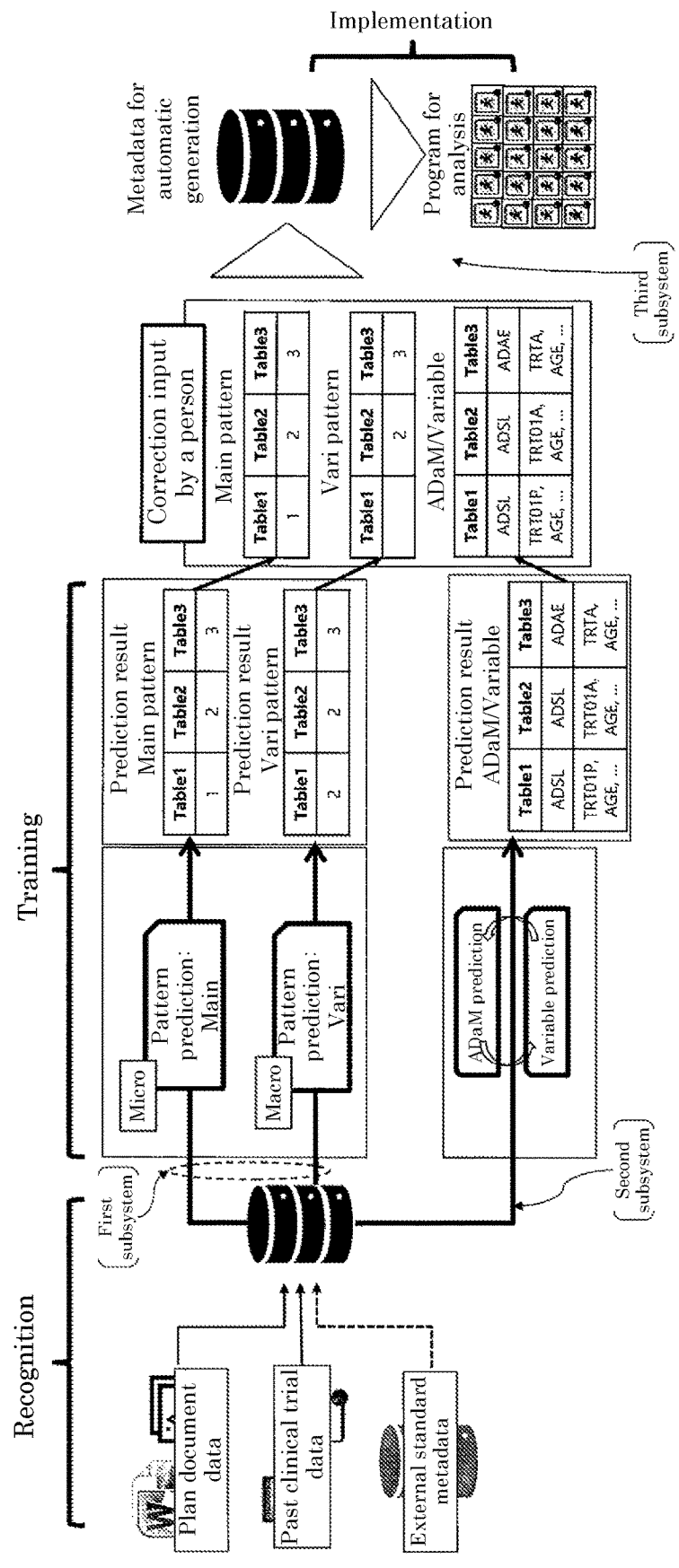
FIG. 2 is a block diagram schematically illustrating all functions of a system of automatically generating a program for preparing an analysis material according to an embodiment.

FIG. 2 is a block diagram schematically illustrating all functions and how processing flows in the system 2 according to an embodiment of the present disclosure. The system 2 according to this embodiment can be roughly divided into the following three functions. A group of functions is referred to as a "function unit" for convenience.

(1) Recognition function unit
(2) Training function unit
(3) Implementation function unit (1) The recognition function unit is configured to acquire information necessary for generating a program for preparing an analysis material from an image/table analysis plan (plan document data) of a target clinical trial. At the same time, the recognition function unit collects and stores labelled training data and results data from past clinical test data and external standard metadata. The external standard data includes, for example, CDISC standard-related data.

FIG. 4 illustrates an example of an image/table analysis plan (part) of an analysis material, which is an image/table plan.

(2) The training function unit is configured to predict and search for information necessary for generating a program for preparing an analysis material of a target clinical trial on the basis of the labeled training data and results data.

(3) The implementation function unit is configured to be able to input, by a human system user, correction data to the information predicted and searched by the training function unit as necessary. Note that the correction data is not necessarily input. Subsequently, the implementation function unit creates metadata for automatic generation on the basis of the predicted and searched information containing the correction data and the information acquired from the image/table analysis plan of the target clinical trial. The implementation function unit further generates an analysis program from a template program while using the metadata created for automatic generation.

Meanwhile, the system 2 according to this embodiment is generally constructed by the following three subsystems.

[First Subsystem] A first program generation assisting system that predicts each form pattern.
[Second Subsystem] A second program generation assisting system that predicts model data and variables.
[Third Subsystem] An analysis program generation system.

In relation to the function units, the first and second subsystems correspond to the training function unit that uses the processing results of the recognition function unit, and the third subsystem corresponds to the implementation function unit that uses the processing results of the training function unit.

Note that the "form" in the analysis material indicates individual analysis results, and is represented by, for example, a table, a listing, and/or a figure. The model data is, for example, ADaM data, and is a set of data and metadata for analysis. The variables are variables in the model data (ADAM data).

Note that the recognition function unit, the training function unit, and the implementation function unit described above do not need to be realized by one, that is, common hardware. Each of the recognition function unit, the training function unit, and the implementation function unit may be realized using separate and independent hardware.

In addition, the system 2 does not always need to include all of the first to third subsystems described above. For example, the system 2 includes the first and second subsystems, but does not necessarily include the third subsystem. At this time, the third subsystem may be realized by a separate computer system. However, a computer system including only the third subsystem is also within the scope of the system 2 according to this embodiment. Further, the first and second subsystems may also be implemented by separate computer systems.

The first subsystem is based on the "format information and layout information" and the "image data" of the image/table analysis plan to predict a form pattern by using two approaches including the first candidate prediction method "micro rule-based prediction" and the second candidate prediction method "macro CNN-based prediction". This system leads to ground truth (i.e., corrected) input assistance by a person.

The second subsystem performs model data/variable prediction by using "text data (format information and layout information)" of the image/table analysis plan, "ADaM specification information" of the ADAM data set specification, which is a model specification, and "model data/variable association information (ADaM/variable association information)" of link information between model data (ADaM data) and variables in past clinical trial forms. The second subsystem then presents a combination of model data/variable prediction and pattern prediction. This system leads to ground truth (i.e., corrected) input assistance by a person.

In the third subsystem, correction data is input, by a human system user, to information predicted and searched by the first subsystem and the second subsystem. Subsequently, the third subsystem creates metadata for automatic generation on the basis of the predicted and searched information containing correction data and the information acquired from the image/table analysis plan of the target clinical trial, and further generates an analysis program from a template program while using the metadata created for automatic generation.

Note that the ADAM data set specification (ADaM specification) in the present disclosure is a model specification about a data model. The ADAM data set specification (ADaM specification) is a specification indispensable when the ADAM data is created by programming, and includes the definition of each variable. FIG. 13 is part of an ADaM data set specification (ADaM specification). FIG. 13 (1) is a definition part of the data set, FIG. 13 (2) is a definition part of the variables, and FIG. 13 (3) is a definition part of the code list.

How the first program generation assisting system (first subsystem) (FIG. 2) for predicting a form pattern works will be described.

Figure 8:
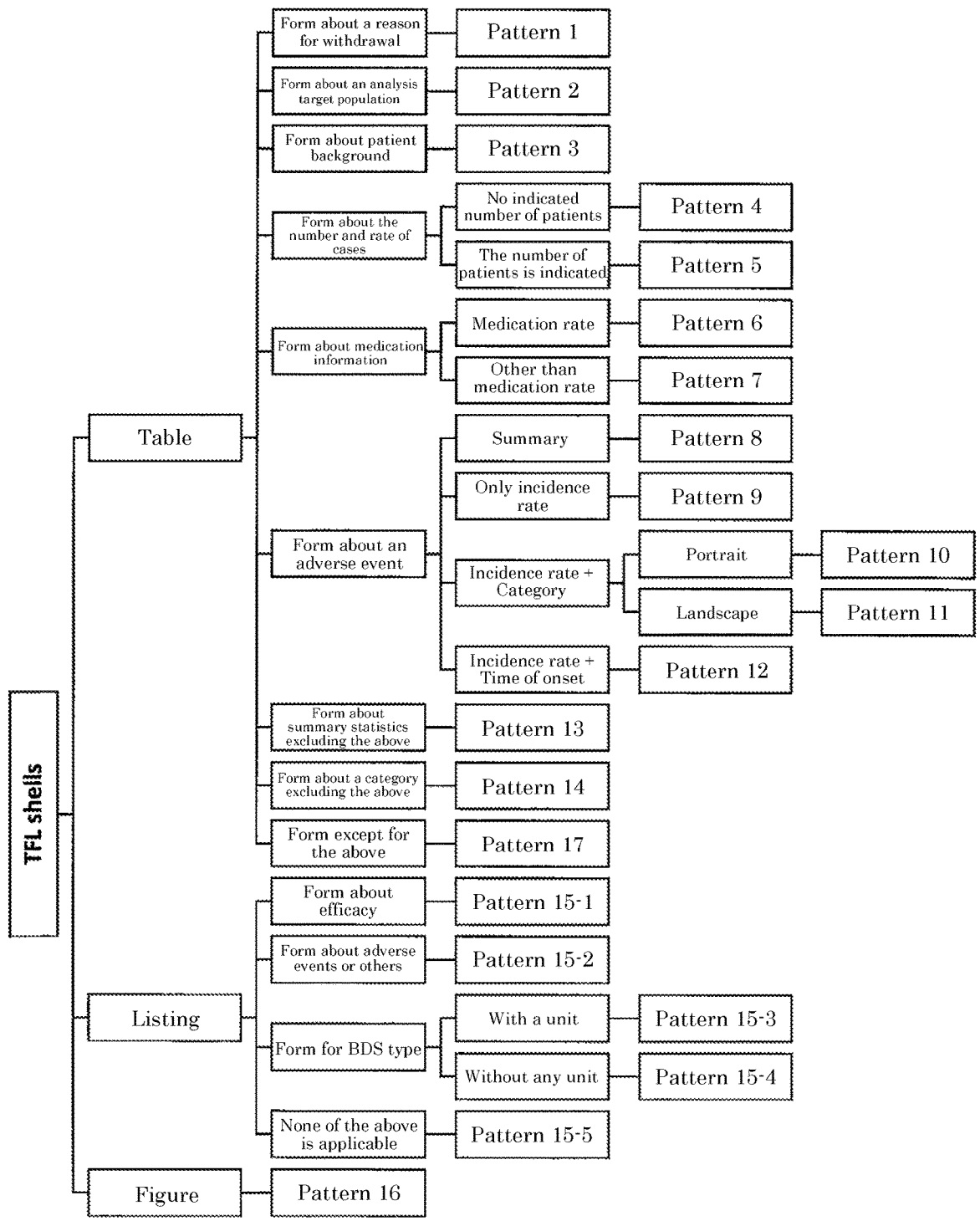
FIG. 8 is an example of patterns in the analysis material.

FIG. 8 is a diagram illustrating a pattern classification example in each analysis material form. Each pattern is basically classified focusing on the content (properties and attributes) indicated by the material. For example, they are classified according to the following viewpoints (a) to (e). In the classification example illustrated in FIG. 8, the patterns are hierarchically classified into 21 patterns (pattern 1 to pattern 16).

(a) Type of form: Table, listing, figure
(b) Content of form: Background information, efficacy information, safety information
(c) Method of analysis: Summary statistics (e.g., the mean, the standard deviation), category count (the number of cases, the percentage)
(d) Structure of database used
(e) Others (e.g., the presence or absence of unit, type of analysis item)

In short, the patterns in the form of the analysis material are classified in advance according to the method of analyzing the clinical trial and the output format of the analysis result.

The first program generation assisting system predicts a classification candidate as to which of 21 patterns a form pattern of interest fits.

Figure 5:
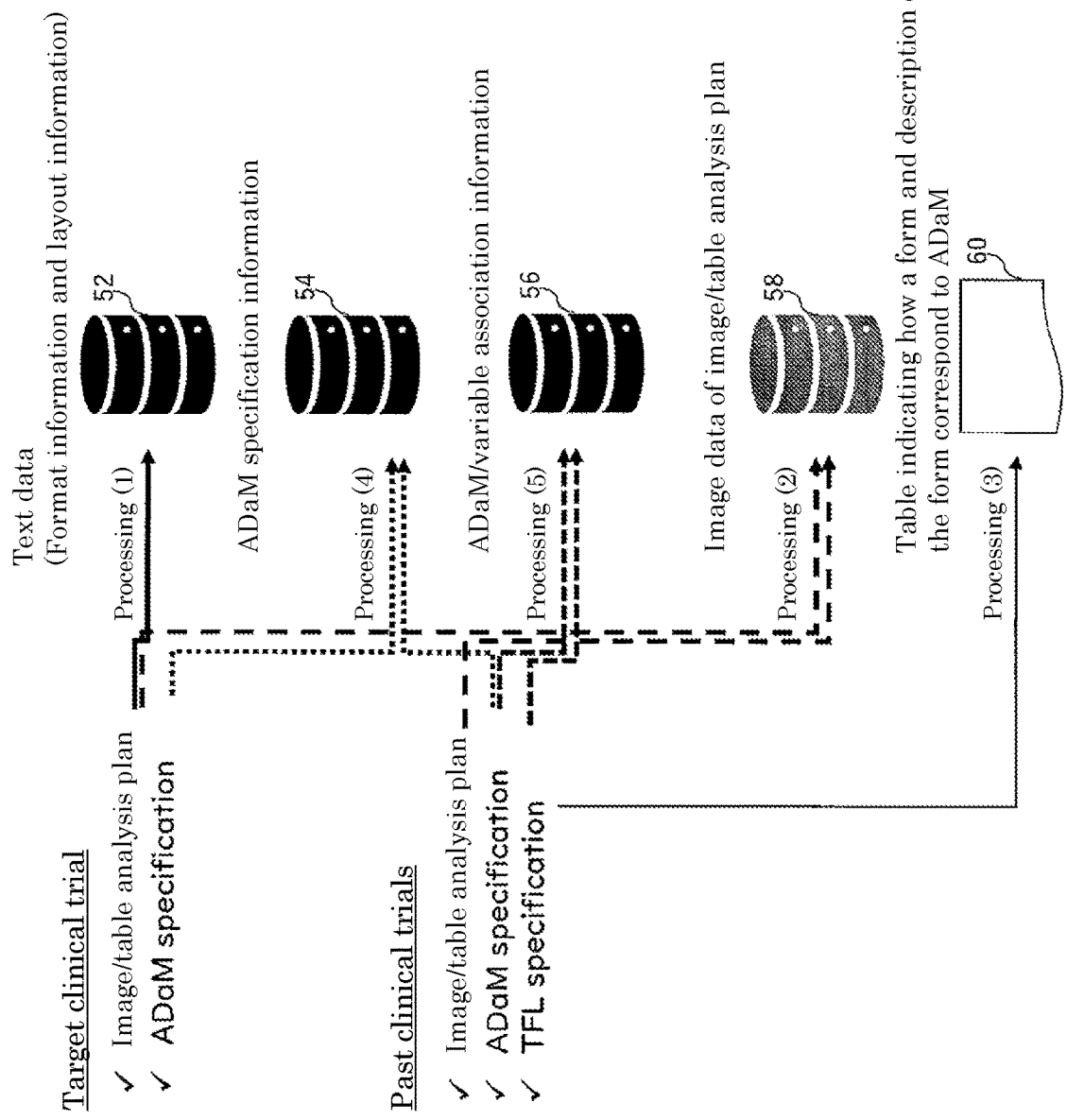
FIG. 5 is a diagram illustrating how data flows in a recognition function unit.

FIG. 5 is a diagram illustrating how data flows generally in the recognition function unit. Among these data, the recognition function unit extracts information necessary for generating a program for preparing an analysis material from the provided image/table analysis plan of the target clinical trial, and creates text data (format information and layout information) 52 (see processing (1) of FIG. 5). The first program generation assisting system acquires the text data (format information and layout information) 52 and executes subsequent processing. Note that the first program generation assisting system may perform processing of creating the text data (format information and layout information) 52.

In addition, the recognition function unit creates image data 58 for use in the CNN from the provided image/table analysis plan of the target clinical trial and the image/table analysis plans of the past clinical trials (see processing (2) of FIG. 5). The first program generation assisting system acquires the image data 58 and executes subsequent processing.

The text data 52 created in (processing (1)) includes "format information" and "layout information". FIGS. 9A and 9B illustrate part of an example of the text data. FIG. 9A represents a "cell_info sheet", which is "format information", and FIG. 9B represents a "layout_info sheet", which is "layout information".

In the "cell_info sheet", which is "format information", for example, data as shown in Table 1 below is recorded as a part.

TABLE 1

PRODUCT: Investigational product number
PROTOCOL: Study name
TYPE_TLF_CONTENTS: Output format (table, listing, figure)
TLF_DISPLAY_ID: Form No.
COLUMN_NO: Column Number (starting from 0)
ROW_NO: Row number (starting from 0)
CELL_DATA: Information included in the relevant cell indicated by the column and row
IS_GROUP: Does it correspond to drug group information? (Yes: 1, No: 0)
IS_CATEGORY: Does it correspond to a variable prediction target? (Yes: 1, No: 0)
ALL_SINGLE_ROW_LAST_IDX: The row number with a solid line at the end In the "layout_info sheet", which is "layout information", for example, data as shown in Table 2 below is recorded as a part.

TABLE 2

PRODUCT: Investigational product number
PROTOCOL: Study name
TYPE_TLF_CONTENTS: Output format (table, listing, figure)
TLF_DISPLAY_ID: Form No.
TITLE: Form title
FOOTNOTE: Form footnote (not every form has a footnote)
PROGRAMMING: Notes on programming
POPULATION: Analysis target group (information described in the second line of each form)
COLUMNS_WIDTH: Width of column in the table (unit: cm)
COLUMNS_ALIGN: Output position of characters and others in a column of the table
(L: left adjustment, C: center adjustment)
SECTION_ORIENT: Orientation of paper at the time of output
(landscape: horizontal, portrait: vertical)

FIGS. 11(1) and (2) exemplify image data created in (processing (2)). The format of the image data here may be, for example, png. In the image data of FIGS. 11(1) and (2), the text character strings are also imaged.

Figure 6:
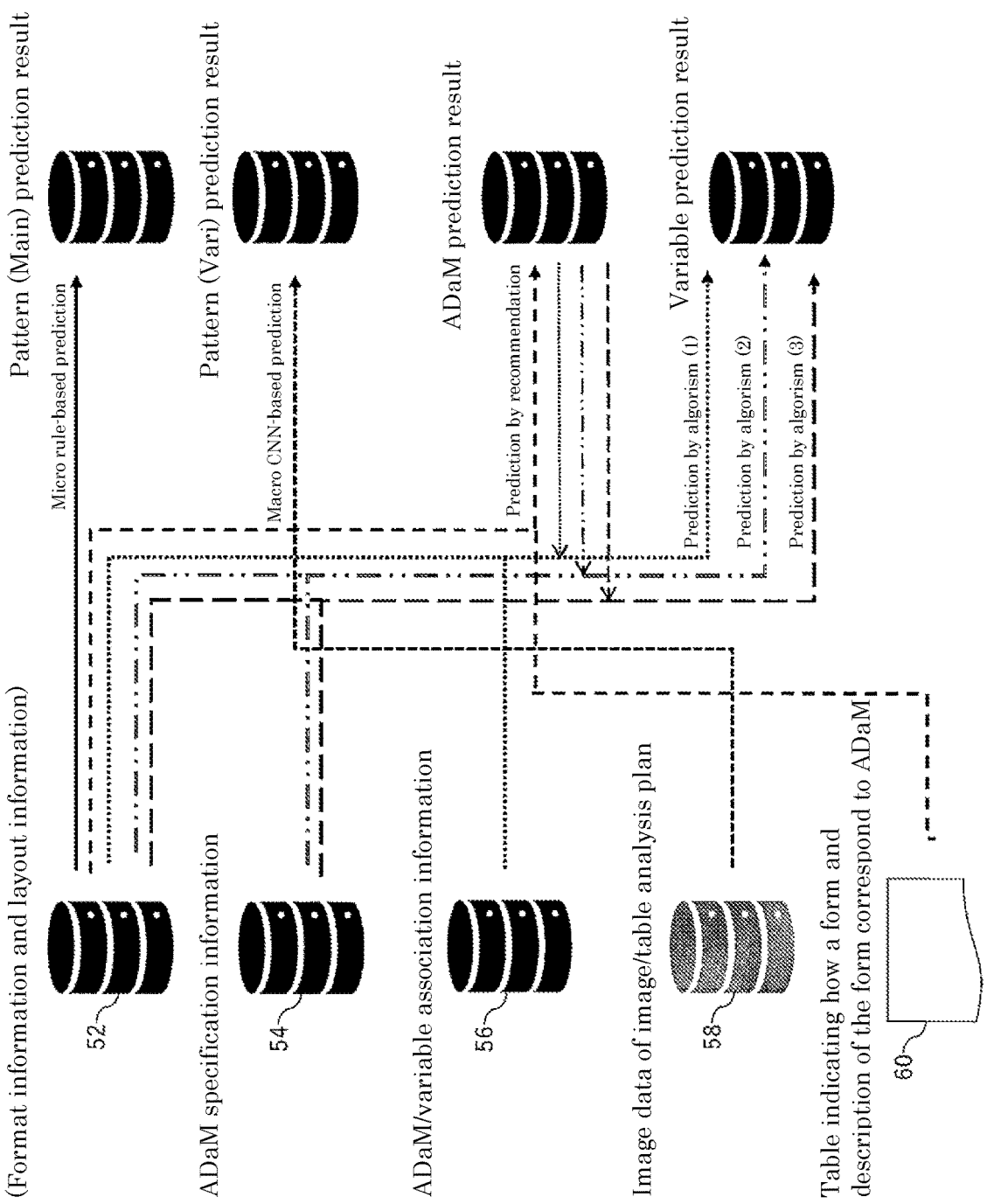
FIG. 6 is a diagram illustrating how data flows in a training function unit.

Next, FIG. 6 is a diagram illustrating how data flows generally in the training function unit. Among these, the first program generation assisting system performs micro rule-based prediction processing by using the acquired text data (format information and layout information) 52, and predicts a form pattern as a classification candidate.

FIG. 10 is a table and collectively provides an example (part) of determination rules for the micro rule-based prediction. Here, 25 conditions for determination (a-1, a-2 . . . up to s) are provided. When each form, particularly, a table number ("form number" in Tables 1 and 2) and a title ("form title" in Table 2) satisfy individual conditions, "Y" is filled in the column of a pattern to be possibly determined. In the first program generation assisting system, the processing circuit 8 (FIG. 1) determines whether or not the text character string included in the acquired text data (format information and layout information) 52 corresponds to the character string included in the above-described determination rule. According to the determination rule indicated in this table, the processing circuit 8 outputs a pattern prediction result (hereinafter, referred to as a "pattern (Main) prediction result") as a classification candidate.

The determination rule defines how each of the plurality of text strings corresponds to the pattern candidate to be classified for each text string. That is, the determination rule defines how the pattern to be classified for each text string corresponds to each of two or more text strings among respective text strings that indicate the reason for withdrawal from the clinical trial, the analysis target population, the patient background, the medication, the adverse event, and/or the efficacy (see FIG. 10).

Note that the determination rules for micro rule-based prediction in the table of FIG. 10 are exemplary, and they may vary.

Further, as illustrated in FIG. 6, the first program generation assisting system performs the macro CNN-based prediction processing by using the acquired image data 58 (see FIG. 11) of the image/table analysis plan, and predicts a form pattern as a classification candidate.

In the macro CNN-based prediction processing, prediction is performed by the following procedure.

(1) Input data for training is prepared from image/table analysis plans of past clinical trials. The target clinical trial is compliant with CDISC (pharmaceutical industry standard criteria for data preparation). Specifically, image data of each form is created from image/table analysis plans of past clinical trials. At the same time, ground truth data indicating a ground truth pattern for each image is prepared.

(2) Next, training data is prepared from the input data for training. Specifically, for example, trimming is performed, and a plurality of pieces of image data are prepared from each piece of image data to obtain the training data. The trimming processing makes it possible to increase the absolute number of pieces of training data. If the absolute number of pieces of training data is sufficient, the input data for training may be used as the training data as it is.

Figure 12:
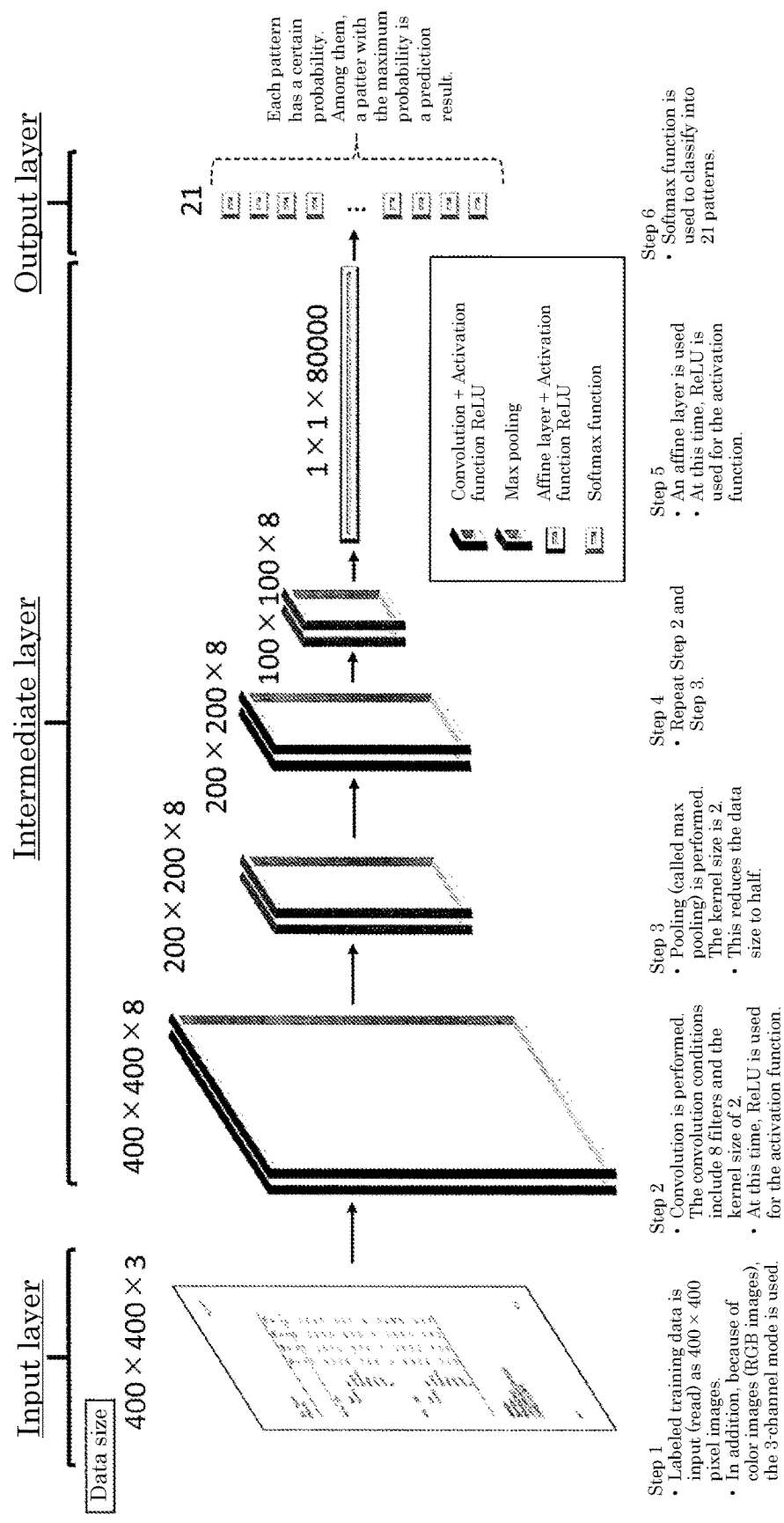
FIG. 12 is an example of a CNN model.

(3) Next, an artificial neural network, for example, a convolutional neural network (CNN) is trained using the training data (2) and the ground truth data (1). FIG. 12 is a conceptual diagram of an example of a CNN used. The size of data input to the input layer, the number of intermediate layers, the size of data input to each intermediate layer, and others are examples. A CNN different from the CNN illustrated in FIG. 12 may be adopted. Of course, an artificial neural network or a learning model other than the CNN may be used.

(4) In the processing of macro CNN-based prediction, as illustrated in FIG. 12, each probability (the total probability of 21 given patterns expressed by 0 to 1 is 1) corresponding to each of 21 given patterns is output for the image data of the image/table analysis plan (see FIG. 11). Further, a pattern with the maximum probability is output as the prediction data. For example, in a certain form A, when the probability of pattern 1 is 0.2, the probability of pattern 2 is 0.78, the probability of pattern 3 is 0.02, and the probabilities of other patterns are 0, the output data of form A is "pattern 2".

The above-described procedures (1) to (3) are processes of training a CNN by using, as labeled training data, image data of each image/table analysis plan of a plurality of past clinical trials and ground truth patterns where the image data of each image/table analysis plan is classified as labelled training data. The procedure (4) is a process for causing a trained artificial neural network constructed on the system as the result of training to classify which form pattern is relevant and infer a classification candidate by using, as the input, the image data (see FIG. 11) of the image/table analysis plan to be classified.

The first program generation assisting system performs at least inference processing. That is, the processing circuit 8 (FIG. 1) inputs image data of the image/table analysis plan to the CNN, acquires a form pattern output from the CNN, and outputs the acquired form pattern as a classification candidate. However, the first program generation assisting system may perform the above-described training process. Here, the processing circuit 8 outputs a pattern prediction result (hereinafter, referred to as the "pattern (Vari) prediction result") as a classification candidate.

FIG. 15 illustrates an example of prediction results in the micro rule-based prediction processing and the macro CNN-based prediction processing. FIG. 15 illustrates an example of the form preparation-related specification (TFL specification) before correction input. This table includes, as classification candidates, the prediction result="Pattern_m" of the micro rule-based prediction processing and the prediction result="Pattern_v" of the macro CNN-based prediction processing for the form number ("Display_identifier") of the form in the image/table analysis plan.

The form preparation-related specification (TFL specification) will be described later.

How the second program generation assisting system (second subsystem) (FIG. 2) for predicting model data and variables works will now be described.

The second program generation assisting system predicts which variable of which model data is used in each form of the analysis material.

Referring again to FIG. 5, FIG. 5 is a diagram illustrating how data flows generally in the recognition function unit. The recognition function unit creates a table 60 indicating how the form and the form description correspond to model data (ADaM data) from a form preparation-related specification (TFL specification) in accumulated past clinical trials (see processing (3) of FIG. 5).

Here, the form preparation-related specification (TFL specification) in the present disclosure is a specification describing, for example, model data, variables, and/or data extraction conditions used during form preparation, and is usually used in programming for preparing a form. FIG. 14 is part of a form preparation-related specification (TFL specification). FIG. 14 (1) illustrates a portion of the specification, and FIG. 14 (2) illustrates a portion of the contents.

In addition, the recognition function unit extracts information necessary for generating a program for preparing an analysis material from an ADaM data set specification (ADaM specification), which is a provided model specification, and creates "ADaM specification information" 54 (see processing (4) of FIG. 5). The ADaM data set specification (ADaM specification), which is a model specification to be provided, includes not only a target clinical trial but also past clinical trials. The "ADaM specification information" 54 is not necessarily created particularly if, for example, the data volume of the ADAM data set specification (ADaM specification) is small.

Further, the recognition function unit creates model data/variable association information (ADaM/variable association information) 56 from a form preparation-related specification (TFL specification) in past clinical trials and an ADaM data set specification (ADaM specification), which is a model specification, in past clinical trials (see processing (5) of FIG. 5). The model data/variable association information (ADaM/variable association information) 56 is link information obtained by linking model data (ADaM data) used in forms of analysis materials of past clinical trials and variables that are each an item describing the model data (ADaM data) and used in the corresponding form. In the model data/variable association information (ADaM/variable association information) 56, the model data (ADaM data) used, the variable, and the label information (LABEL) are linked. That is, the ADAM data used for analyzing the label information (LABEL) and the variable are linked. For example, in a case where the label information (LABEL) is "Age", information where "In previous clinical trials, the variable AGE in ADaM=ADSL was used to analyze LABEL=AGE" is stored.

FIG. 19 illustrates an example of the model data/variable association information ("ADaM/variable association information") 56. The data set (Dataset) indicates the name of the model data (ADAM data), the variable (Variable) indicates a variable name, and the label (LABEL) indicates information included in each cell.

Next, referring again to FIG. 6, FIG. 6 is a diagram illustrating how data flows generally in the training function unit. Among them, the second program generation assisting system first outputs prediction of the model data (ADAM data).

That is, the second program generation assisting system calculates the similarity between the description of each form in the image/table analysis plan of the target clinical trial and the description of each form in the analysis materials of the past clinical trials. Further, the second program generation assisting system extracts and recommends, in response to the calculated similarity, names of one or more pieces of model data (ADaM data) used in each form in the analysis materials of the past clinical trials, which form corresponds to each form in the image/table analysis plan of the target clinical trial (see "prediction by recommendation" in FIG. 6).

Here, the "description of each form in the image/table analysis plan of the target clinical trial" is data included in the "format information" of the text data 52 as illustrated in FIGS. 5, 6, and 9A. The "description of each form in the analysis materials of the past clinical trials" is included in the "table 60 indicating how the form and the description of form correspond to ADaM" as illustrated in FIGS. 5 and 6. Further, the names of one or more pieces of model data (ADaM data) used in each form in the analysis materials of the past clinical trials are also included in the "table 60 indicating how the form and the description of form correspond to ADaM" as illustrated in FIGS. 5 and 6.

The above-described similarity between the description of each form in the image/table analysis plan of the target clinical trial and the description of each form in the analysis materials of the past clinical trials may be calculated using a given similarity evaluation function. The given similarity evaluation function is, for example, a Tanimoto coefficient or a Jaccard coefficient. In addition, the description in each form may be, for example, the title of each form.

Figure 17:
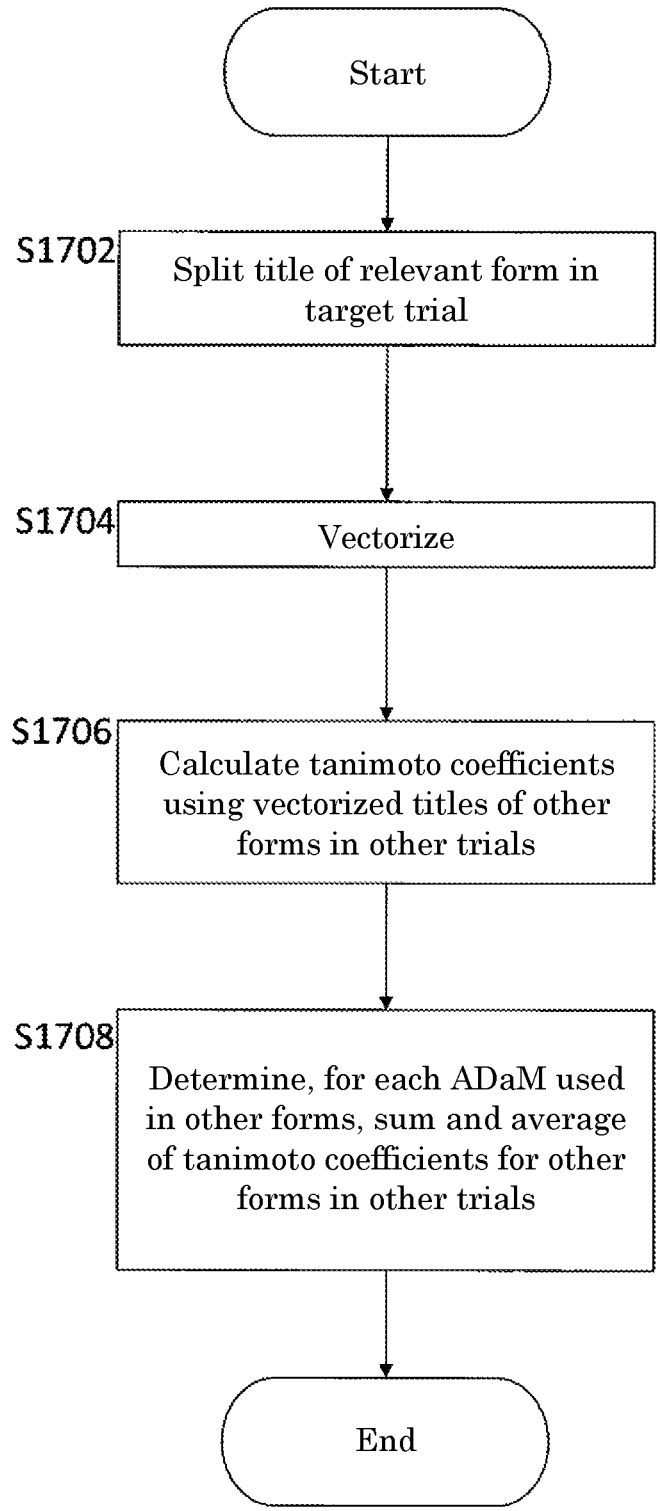
FIG. 17 is a flowchart illustrating an example of an ADaM prediction algorithm.

FIG. 17 is a flowchart illustrating an example of an algorithm of prediction by recommendation for ADaM data. First, the processing circuit 8 (FIG. 1) splits the title of a form (e.g., a table) of the target clinical trial (step S1702). Since the title is normally written in English, in this embodiment, the processing circuit 8 separates the title at the position of blank (blank space) and splits the title into words.

For example, when the title of the form "table X" is "Summary of adverse events", the title is split into "Summary", "of", "adverse", and "events".

Next, the processing circuit 8 vectorizes the split result (step S1704). In the above example, the processing circuit 8 generates a vector as in the following Expression 1.

$$\begin{bmatrix} \text{Summary} \\ \text{of} \\ \text{adverse} \\ \text{events} \end{bmatrix} \quad [\text{Expression 1}]$$

Next, the processing circuit 8 obtains a Tanimoto coefficient between the split result and the title of another form of another past clinical trial, which title has been vectorized (step S1706).

For the Tanimoto coefficient for other forms in the other past clinical trials, the sum and the average are determined for each ADaM data used in the other forms (step S1708). Eventually, the ADAM data where the average is not zero is extracted and recommended together with the average. Note that the larger the average, the higher the degree of recommendation of the ADAM data.

Note that the Tanimoto coefficient related to the title in the form "table A" and the form "table B" is usually calculated as follows.

TABLE 3

Tanimoto coefficient (T) for Table A and Table B

| | |
|---|---|
| $n_{11}$ | The number of words included in both the title of Table A and the title of Table B |
| $n_{10}$ | The number of words included only in the title of Table A |
| $n_{01}$ | The number of words included only in the title of Table B |

$$T = \frac{n_{11}}{n_{11} + n_{10} + n_{01}}$$

Next, as illustrated in FIG. 6, the second program generation assisting system outputs prediction of variables. Each variable prediction is performed according to the following three algorithms. All the variables predicted by the respective three algorithms are output as candidates for the prediction result.

(1) Prediction by algorithm (1)
(2) Prediction by algorithm (2)
(3) Prediction by algorithm (3)

(1) Prediction by Algorithm (1)

Figure 18:
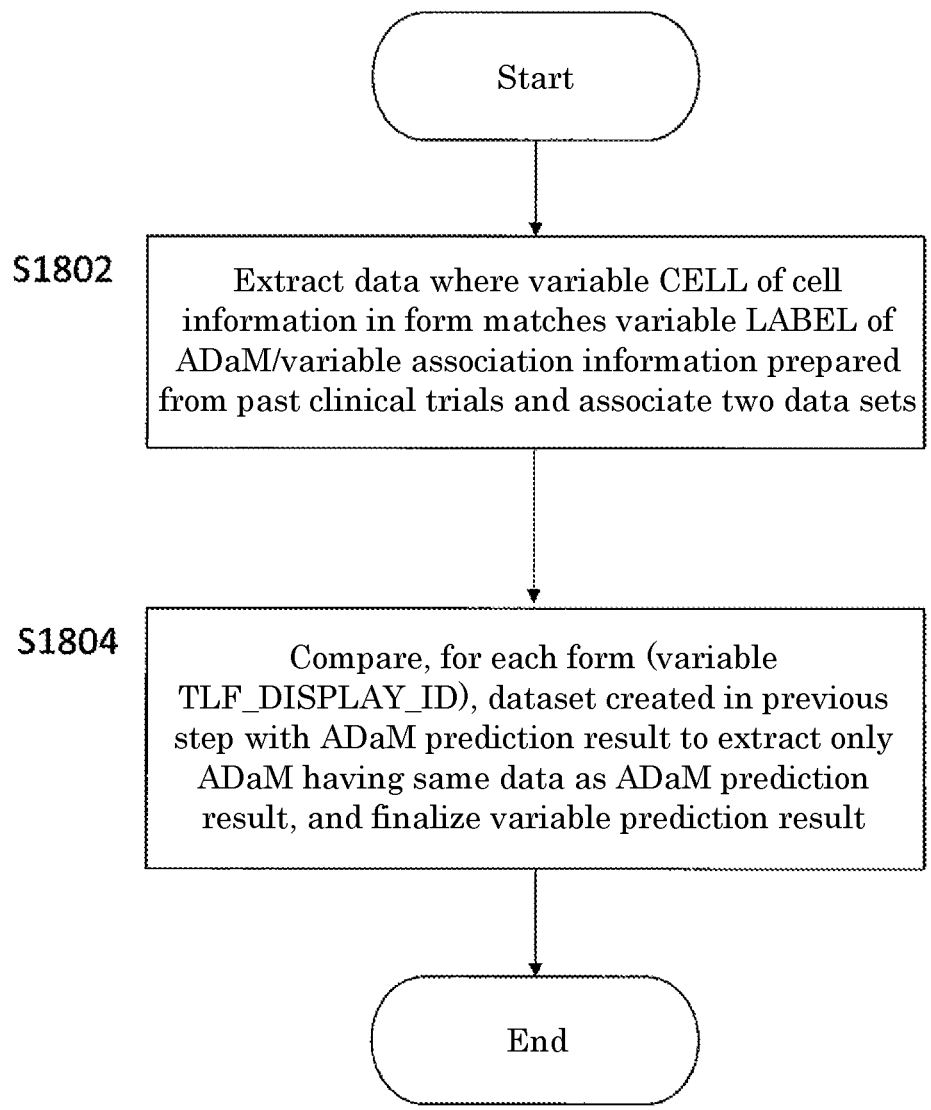
FIG. 18 is a flowchart illustrating an algorithm (1) for predicting a variable.

FIG. 18 is a flowchart illustrating an algorithm (1) for predicting a variable. First, the processing circuit 8 (FIG. 1) extracts data in which the "variable CELL of the cell information in the form" in the "format information" of the text data 52 matches the variable LABEL in the model data/variable association information (ADaM/variable association information) 56 (see processing (5) of FIG. 5)) prepared from the past clinical trials. Then, the processing circuit 8 (FIG. 1) creates an associated form obtained by associating the two data sets through the two data matched (step S1802). As a result, the cell information in the form of the target clinical trial, the model data (ADaM data), and the variable are associated.

Next, the processing circuit 8 compares the associated form created in the previous step (step S1802) with the prediction result (see FIG. 6) of the model data (ADaM data) for each form (form number). Then, the processing circuit 8 extracts only data that matches the prediction result of the model data (ADAM data) from the comparison result, and finalizes the variable prediction result (step S1804). That is, the processing circuit 8 (FIG. 1) compares the prediction result of the model data (ADaM data) with the prediction result of the variable, and narrows and recommends the variable. At this time, the adopted variable, in addition to the name of the extracted model data (ADaM data), is output as a candidate.

(2) Prediction by Algorithm (2)

Figure 20:
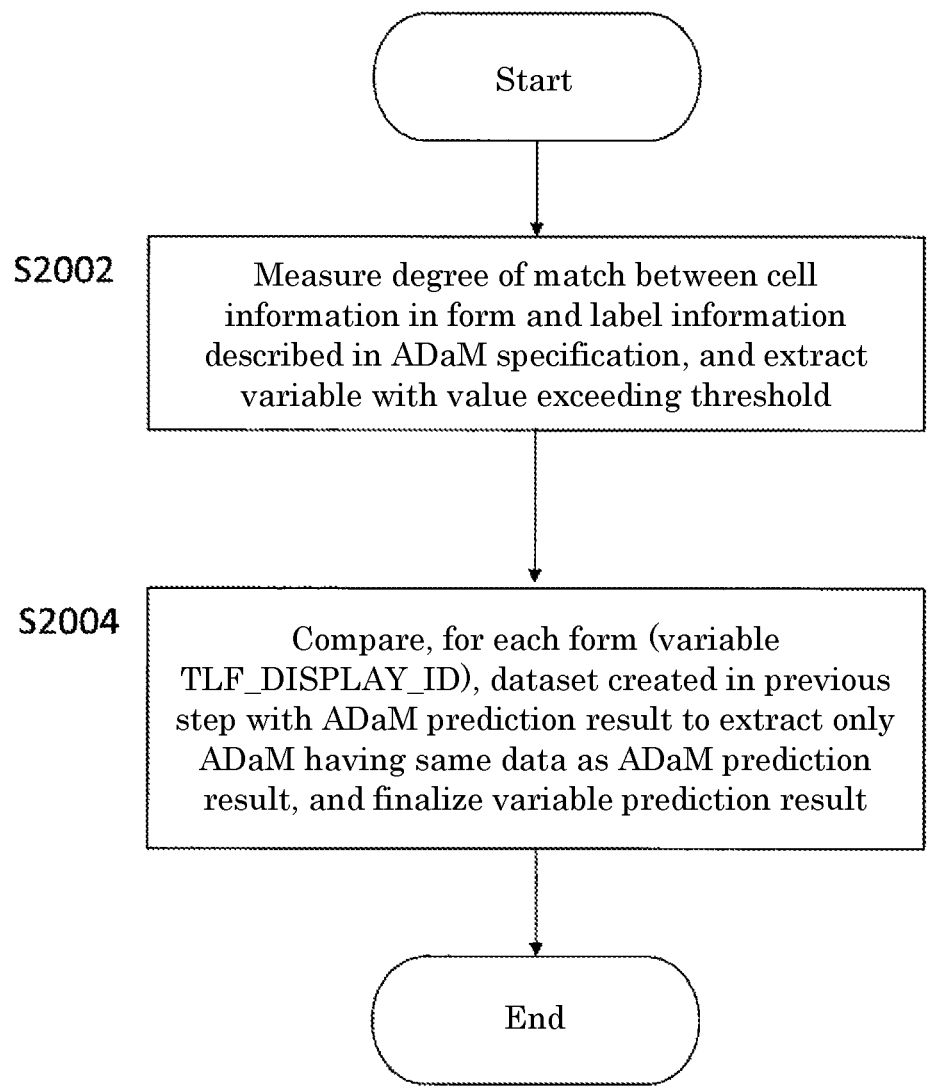
FIG. 20 is a flowchart illustrating an algorithm (2) for predicting a variable.

FIG. 20 is a flowchart illustrating an algorithm (2) for predicting a variable. First, the processing circuit 8 (FIG. 1) measures the degree of match between the "variable CELL of the cell information in a form" in the "format information" of the text data 52 and a given item indicating the variable described in the "ADaM specification information" 54, and extracts a variable of which the degree of match exceeds a threshold (step S2002). The threshold is, for example, 0.7.

The given item only needs to indicate a variable, and here, the given item is label information of the variable. The label indicates the name of the variable, and for example, in the case of a variable SITEID, the label is "Study Site Identifier". When cell information in a form of the target clinical trial includes a word such as "Site", it is predicted that the degree of match is high and the probability of using the variable SITEID is high in the form. In FIG. 13 showing part of the ADAM data set specification (ADaM specification), FIG. 13 (2) shows part of the variable definition portion "variable sheet", and the fourth column shows the variable name, and the fifth column shows the label.

The degree of match only needs to indicate the degree of matching between two words, and may be calculated using, for example, an N-gram. In general, the N-gram is a method of dividing a target character string into every N characters (e.g., every N=2 characters) to index the character string. Hereinafter, the degree of match between "SAFFL" and "COMPFL" is calculated, for example, under the condition of N=2.

First, the processing circuit 8 divides "SAFFL" or "COMPFL" into every 2 (=N) characters to create respective character string groups. The following [Expression 2] is a character string group of "SAFFL", and [Expression 3] is a character string group of "COMPFL".

$$\begin{bmatrix} S & A \\ A & F \\ F & F \\ F & L \end{bmatrix} \quad \text{[Expression 2]}$$

$$\begin{bmatrix} C & O \\ O & M \\ M & P \\ P & F \\ F & L \end{bmatrix} \quad \text{[Expression 3]}$$

The processing circuit 8 calculates the degree of match based on the number of character strings common to the character string group from "SAFFL" and the character string group from "COMPFL". For example, specifically, the number of common character strings is divided by the number of all combinations (in the above example, the number of combinations is 4×5=20) to calculate the degree of match.

Next, the processing circuit 8 extracts only data that matches the prediction result of the model data (ADAM data) from the data set extracted in the previous step (step S2002) for each form (form number), and finalizes the variable prediction result (step S2004). That is, the processing circuit 8 compares the prediction result of the model data (ADaM data) with the prediction result of the variable, and narrows and recommends the variable. At this time, the adopted variable, in addition to the name of the extracted model data (ADaM data), is output as a candidate.

(3) Prediction by Algorithm (3)

Figure 21:
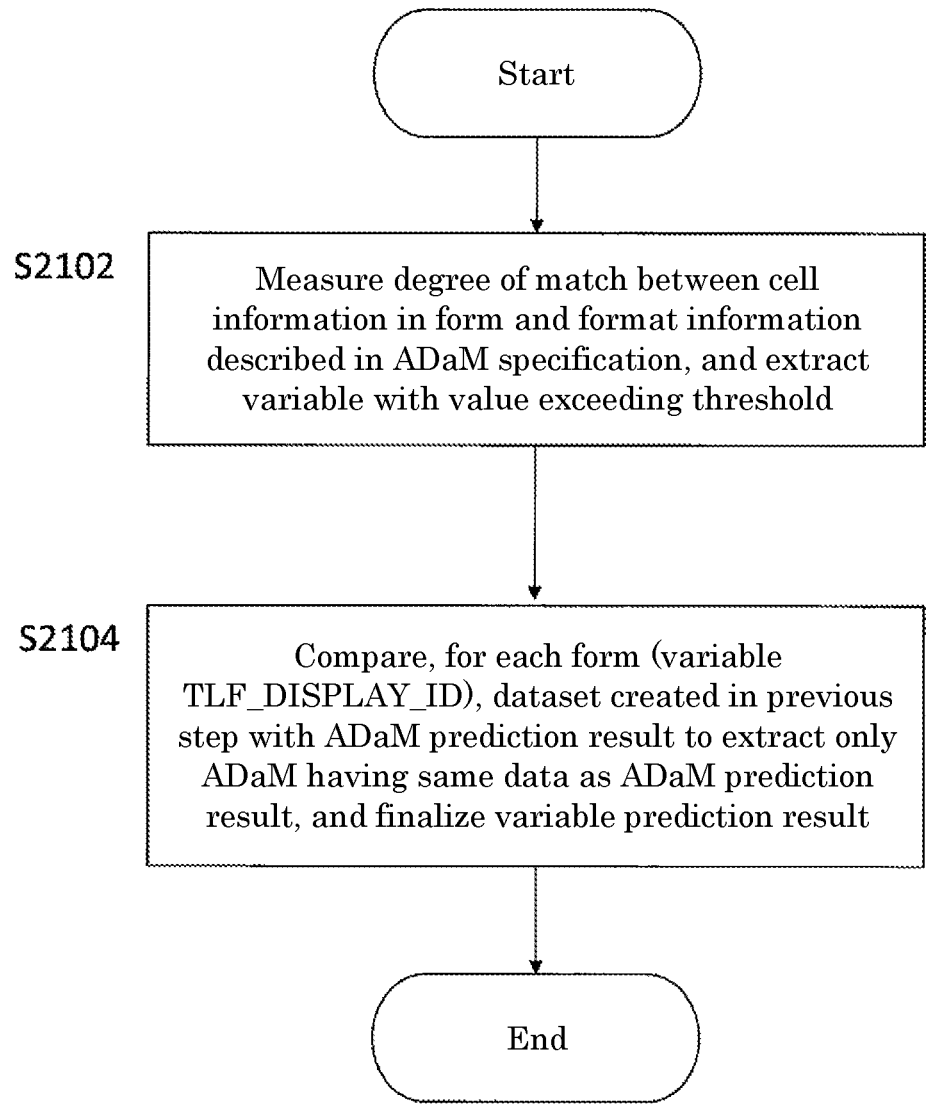
FIG. 21 is a flowchart illustrating an algorithm (3) for predicting a variable.

FIG. 21 is a flowchart illustrating an algorithm (3) for predicting a variable. First, the processing circuit 8 (FIG. 1) measures the degree of match between the "variable CELL of the cell information in a form" in the "format information" of the text data 52 and a second given item indicating the variable described in the "ADaM specification information" 54, and extracts a variable of which the degree of match exceeds a threshold (step S2102). The threshold is, for example, 0.7.

The second given item also only needs to indicate a variable, and here, the second given item is format information of the variable. The format indicates each category of the categorical variable, and for example, in the case of variable SEX, the format is "Male" or "Female". When cell information in a form of the target clinical trial includes information with a high degree of match with "Male" or "Female", it is predicted that the probability of using the variable SEX is high in the form. In FIG. 13 showing part of the ADAM data set specification (ADaM specification), FIG. 13 (3) shows part of the code list definition portion "Codelist sheet", and the first column shows the variable name, and the seventh column shows the format.

The degree of match here only needs to indicate the degree of matching between two words, and may be calculated using, for example, an N-gram as described above.

Next, the processing circuit 8 extracts only data that matches the prediction result of the model data (ADaM data) from the data set extracted in the previous step (step S2102) for each form (form number), and finalizes the variable prediction result (step S2104). That is, the processing circuit 8 compares the prediction result of the model data (ADaM data) with the prediction result of the variable, and narrows and recommends the variable. At this time, the adopted variable, in addition to the name of the extracted model data (ADaM data), is output as a candidate. As for the prediction of the variable by the second program generation assisting system, (1) the prediction by algorithm (1), (2) the prediction by algorithm (2), and (3) the prediction by algorithm (3) have been each described above. In the prediction of the variable by the second program generation assisting system, all the algorithms are not necessarily used for prediction. The prediction may be performed by at least one algorithm among the three algorithms.

An operation of the analysis program generation system (third subsystem) will be described.

The analysis program generation system presents, as a form of the form preparation-related specification (TFL specification) before correction input as illustrated in FIG. 15 to system users, the pattern (Main) prediction result, the pattern (Vari) prediction result, the ADAM model data prediction result, and the variable prediction result (see FIG. 6.), which are information predicted and searched by the first program generation assisting system and the second program generation assisting system.

Figure 7:
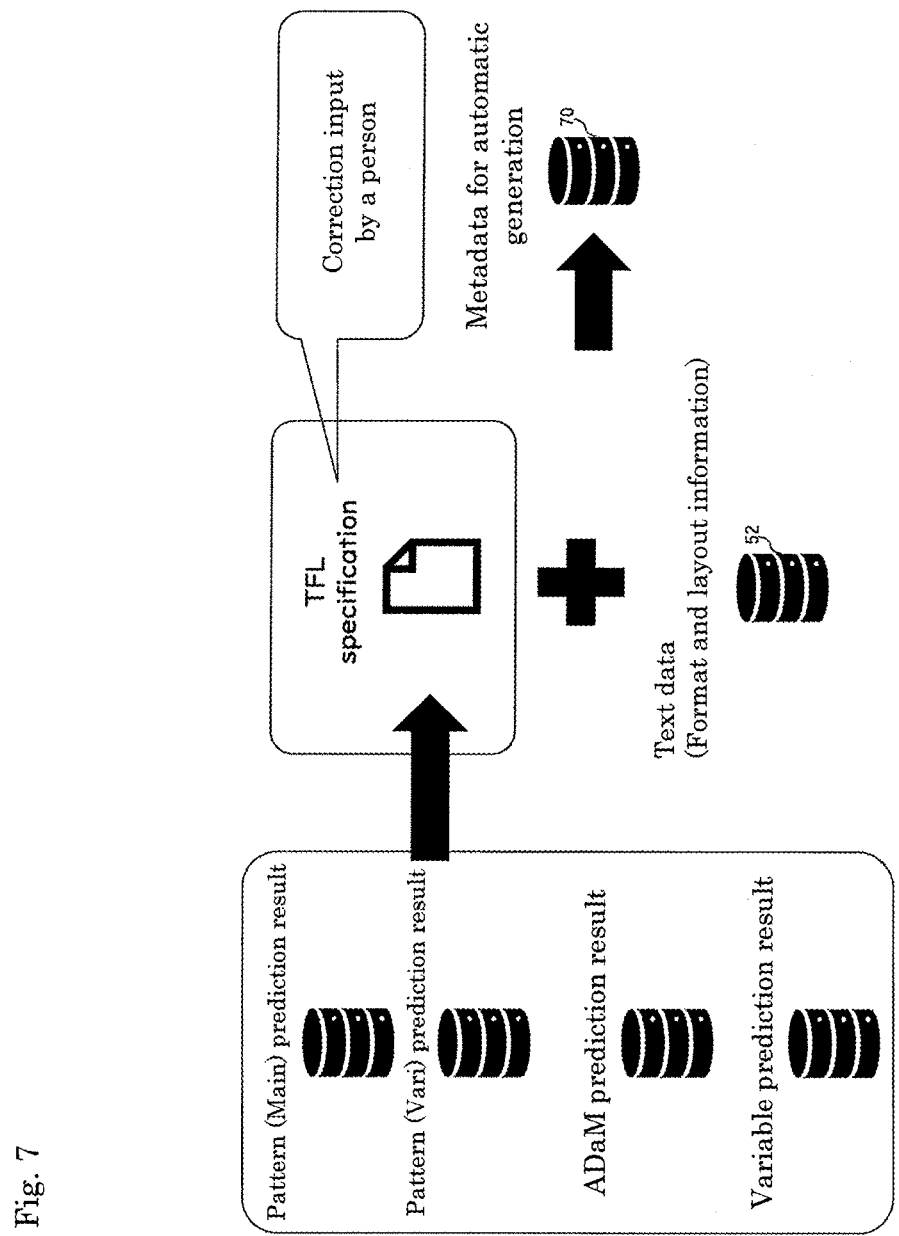
FIG. 7 is a diagram illustrating how data flows from "training" to creation of metadata for automatic generation.

FIG. 7 is a diagram illustrating how data flows from "training" to creation of metadata for automatic generation.

FIG. 15 is an example of the form preparation-related specification (TFL specification) before correction input. This table indicates the prediction result="Pattern_m" (the 7th column) of the micro rule-based prediction processing and the prediction result="Pattern_v" (the 8th column) of the macro CNN-based prediction processing, the ADAM (model data) prediction result="P_Dataset" (the 9th column), and the variable prediction result="P_Analysis variable" (the 10th column) for the form number ("Display_identifier" in the 2nd column) of the form in the image/table analysis plan.

The system user inputs the correction data to these data. FIG. 16 is an example of the form preparation-related specification (TFL specification) after correction input. Note that there may be no points to be corrected. In this case, no correction data is input, and data of the form preparation-related specification (TFL specification) before correction input is used as it is.

Next, the analysis program generation system creates metadata 70 for automatic generation on the basis of the form preparation-related specification (TFL specification) with correction data reflected and "layout information" for specifying the output format of the analysis result in the text data (format information and layout information) 52 for a form of the target clinical test (see FIG. 7). FIG. 22 is an example of metadata 70 for automatic generation. The metadata 70 for automatic generation includes pattern-specifying data for specifying a pattern in a form of the analysis material.

Next, the analysis program generation system uses a template program that is stored in the storage device 12 and corresponds to each of the plurality of patterns in the form of the analysis material, the template program being capable of specifying the method of analyzing the clinical trial and the output format of the analysis result. That is, the analysis program generation system reads the template program corresponding to each pattern specified by the pattern-specifying data in the metadata 70 for automatic generation. Further, the analysis program generation system automatically generates an analysis program from the read template program by using the metadata 70 for automatic generation. FIG. 23 is an example of the template program.

Here, the text data (format information and layout information) 52 for the target clinical test form includes an instruction of the output format of the analysis result as described above. Thus, the analysis program generation system instructs, to the corresponding template program, the output format of the analysis result on the basis of the text data 52, and automatically generates an analysis program capable of outputting the analysis result in the layout according to the instructed output format.

The first program generation assisting system for assisting generation of a program for analyzing a clinical trial according to an embodiment of the present invention includes: the interface device 6 configured to acquire text data and image data created from an image/table analysis plan that specifies a method of analyzing a clinical trial and an output format of an analysis result; and the storage device 12 configured to store the text data and the image data; and the processing circuit 8 configured to execute each of a first candidate prediction method using the text data and a second candidate prediction method using the image data to classify the image/table analysis plan into at least one pattern among a plurality of predetermined patterns, and then to output a result as a classification candidate. The plurality of patterns are classified in advance according to the clinical trial analyzing method and the analysis result output format. The first program generation assisting system is provided in advance with a determination rule that defines a relationship of how each of a plurality of text strings corresponds to a pattern in which each text string is classified. Also, provided is a trained artificial neural network constructed by training with, as labeled training data, image data of each image/table analysis plan from a plurality of past clinical trials and ground truth patterns obtained by classifying the image data of each image/table analysis plan. The processing circuit 8 uses the text strings included in the text data of the image/table analysis plan and the determination rule to output data indicating the first pattern among the plurality of patterns by executing the first candidate prediction method. Then, the processing circuit 8 inputs the image data of the image/table analysis plan into the artificial neural network to acquire data indicating the second pattern output from the artificial neural network by executing the second candidate prediction method. Further, the processing circuit 8 outputs the first pattern and the second pattern as classification candidates for the analysis material.

In addition, the second program generation assisting system for assisting generation of a program for analyzing a clinical trial according to an embodiment of the present invention includes: the storage device 12 configured to store the database 16; the interface device 6 configured to acquire data about an image/table analysis plan that specifies a method of analyzing a clinical trial and an output format of an analysis result; and the processing circuit 8 configure to output, as a candidate, a name of at least one model data to be used for analyzing the clinical trial with reference to the database 16 and the data about the image/table analysis plan. The image/table analysis plan includes one or more forms, and each form specifies analysis content for each type of analysis of the clinical trial. The database 16 stores each form of analysis materials in past clinical trials and a name of model data used in each form, namely a name of model data that is a collection of a data set and metadata for analysis. The processing circuit 8 uses a given similarity evaluation function to calculate, for each form of the image/table analysis plan obtained, a similarity between description in the form and description in each form of analysis materials in past clinical trials. Further, the calculated similarity is used to extract a name of at least one piece of the model data used in the form of analysis materials in past clinical trials, which name corresponds to the former description in the form, and then output the extracted model data name.

Furthermore, in the second program generation assisting system for assisting generation of a program for analyzing a clinical trial according to an embodiment of the present invention, the database 16 stores link information in which model data used in a form of analysis materials of past clinical trials and a variable that is an item describing the model data and used in the form are linked. The processing circuit 8 compares the first item of the text data in each form of the image/table analysis plan with the second item of the variable in the link information. In the case of match, the processing circuit 8 creates an associated form in which the first item of the text data in each form of the image/table analysis plan and the second item of the variable in the link information are used for association. The associated form may include model data having the same name of the extracted model data. In this case, the processing circuit 8 adopts, as a variable of the extracted model data, a variable that is an item describing the model data having the same name in the associated form. Then, the processing circuit 8 outputs, in addition to the name of the extracted model data, the adopted variable as a candidate.

Further, in the second program generation assisting system for assisting generation of a program for analyzing a clinical trial according to an embodiment of the present invention, the interface device 6 further acquires data about the model specification in which the model data prepared in the clinical trial and the definition of the variable describing the model data are associated and described. The processing circuit 8 calculates the degree of match between the first item of text data in each form of the image/table analysis plan and the third item indicating a variable described in the model specification by using a given algorithm. The processing circuit 8 then selects, from the model specification, model data associated with a variable with a larger degree of match calculated than a predetermined threshold. The selected model data may match the extracted model data. In this case, the processing circuit 8 adopts a variable larger than the threshold as a variable of the extracted model data. Then, the processing circuit 8 outputs, in addition to the name of the extracted model data, the adopted variable as a candidate.

The analysis program generation system for generating a program for analyzing a clinical trial according to an embodiment of the present invention includes the interface device 6, the storage device 12, and the processing circuit 8. The interface device 6 is configured to acquire the first pattern and the second pattern output from the first program generation assisting system, and acquire the name and the variable of the model data output from the second program generation assisting system. The interface device 6 may acquire correction data for correcting the first pattern, the second pattern, the name, and/or the variable. The storage device 12 is configured to store a template program corresponding to each of the plurality of patterns and capable of specifying the method of analyzing the clinical trial and the output format of the analysis result. In a case where correction data is acquired, the processing circuit 8 uses the corrected first pattern, second pattern, name and/or variable and the text data. In a case where no correction data is acquired, the processing circuit 8 uses the acquired first pattern, second pattern, name and/or variable, and the text data. Based on these data, the processing circuit 8 creates metadata including pattern-specifying data that specifies one of the plurality of patterns. Further, the processing circuit 8 reads a template program corresponding to each pattern specified by the pattern-specifying data, and uses the metadata to generate an analysis program from the template program.

The system of automatically generating a program for preparing an analysis system includes the first program generation assisting system, the second program generation assisting system, and the analysis program generation system according to embodiments of the present invention as described above. This system can assist automated programming for automatic generation of an analysis material prepared by analysis work in a clinical trial during pharmaceutical development, and makes it possible to automatically generate a program for preparing an analysis material.

The embodiments have been described above as examples of the technologies disclosed in the present application. However, the technologies in the present disclosure are not limited thereto, and are also applicable to embodiments with, for instance, changes, replacements, additions, and/or omissions, if appropriate.

The analysis program generation system according to the above-described embodiments uses the pattern (Main) prediction result, the pattern (Vari) prediction result, the ADaM model data prediction result, and the variable prediction result (see FIG. 6.), which are information predicted and searched by the first program generation assisting system and the second program generation assisting system. This leads to creation of the metadata 70 for automatic generation, which metadata is used to automatically generate an analysis program. Here, for example, clinical trial-related data using ADaM, which data accurately complies with the CDISC standard, may be sufficiently accumulated and provided as training data. In this case, the ADaM model data and variable predictions become unnecessary. Then, the output data of the first program generation assisting system and the ADaM and variable search results may be used, resulting in creation of the metadata 70 for automatic generation. That is, the metadata 70 for automatic generation may be created from the pattern (Main) prediction result, the pattern (Vari) prediction result, and the ADaM and variable search results.

Meanwhile, the accompanying drawings and the detailed description have been provided in order to describe the embodiments. Thus, the components described in the accompanying drawings and the detailed description may include not only components essential for solving the problem but also components that are dispensable for solving the problem in order to illustrate the above technologies. Therefore, it should not be immediately recognized that these dispensable components are essential based on the fact that these dispensable components are described in the accompanying drawings and the detailed description.

Besides, since the above-described embodiments are intended to illustrate the technologies in the present disclosure, various changes, replacements, additions, omissions, and/or other modifications can be made within the scope of the claims or equivalents thereof.

REFERENCE SIGNS LIST

2 . . . . System of automatically generating a program for preparing an analysis material
4 . . . . Computer device
6 . . . . Interface device
8 . . . . Processing circuit
10 . . . . Memory
12 . . . . Storage device
14 . . . . External network
16 . . . . Database
52 . . . . Text data (format information and layout information)
54 . . . . ADaM specification information
56 . . . . Model data/variable association information ("ADaM/variable association information")
58 . . . . Image data of an image/table analysis plan
60 . . . . Table indicating how a form and the description of form correspond to ADaM
70 . . . . Meta data for automatic generation

The invention claimed is:

1. A program generation assisting system for assisting generation of a program for analyzing a clinical trial, the system comprising:
   an interface device configured to acquire text data and image data created from an image/table analysis plan that specifies a method of analyzing the clinical trial and an output format of an analysis result;
   a storage device configured to store the text data and the image data; and
   a processing circuit configured to execute each of a first candidate prediction method using the text data and a second candidate prediction method using the image data to classify the image/table analysis plan into at least one pattern among a plurality of predetermined patterns, and then to output a result as a classification candidate,
   wherein the plurality of patterns are classified in advance according to the clinical trial analyzing method and the analysis result output format,
   wherein the program generation assisting system has in advance a determination rule defining a relationship of how each of a plurality of text strings corresponds to a pattern in which each text string is classified, and has a trained artificial neural network constructed by training with, as labeled training data, image data of each image/table analysis plan from a plurality of past clinical trials and ground truth patterns obtained by classifying the image data of each image/table analysis plan, and wherein the processing circuit is configured to use text strings included in the text data of the image/table analysis plan and the determination rule to output data indicating a first pattern among the plurality of patterns by executing the first candidate prediction method, input the image data of the image/table analysis plan into the artificial neural network to acquire data indicating a second pattern output from the artificial neural network by executing the second candidate prediction method, and ouput the first pattern and the second pattern as the classification candidates of an analysis material.

2. The program generation assisting system according to claim 1, wherein the determination rule defines how the pattern to be classified for each text string corresponds to each of two or more text strings among respective text strings that indicate a reason for withdrawal from the clinical trial, an analysis target population, patient background, medication, an adverse event, and/or efficacy.

3. The program generation assisting system according to claim 1, wherein the artificial neural network is a convolutional neural network.

4. The program generation assisting system according to claim 3, wherein the convolutional neural network is configured to calculate a probability where the image data of the image/table analysis plan corresponds to each of the plurality of patterns.

5. The program generation assisting system according to claim 4, wherein the convolutional neural network is further configured to output data indicating a pattern having a maximum probability among probabilities corresponding to the respective patterns.

6. An analysis program generation system for generating a program for analyzing a clinical trial, the system comprising:
an interface device;
a storage device; and
a processing circuit,
wherein the interface device is configured to:
acquire the first pattern and the second pattern output from the program generation assisting system according to claim 1,
acquire the name and the variable of the model data output from a program generation assisting system including:
a database configured to store link information in which a model data used in the form of analysis materials of past clinical trials and a variable that is an item describing the model data and used in the form are linked to each other; and
a processing circuit configured to compare a first item of text data in each form of an image/table analysis plan with a second item of the variable of link information, generate, in a case of match, an associated form in which the first item of the text data in each form of the image/table analysis plan and the second item of the variable of the link information are used for association, and adopt, when model data having the same name of the extracted model data in the associated form, as a variable of the extracted model data, a variable that is an item describing the model data having the same name in the associated form, and then output, in addition to the name of the extracted model data, the adopted variable as the candidate, and
acquire correction data for correcting the first pattern, the second pattern, the name, and/or the variable, wherein the storage device is configured to store a template program corresponding to each of the plurality of patterns and capable of specifying a method of analyzing the clinical trial and an output format of an analysis result, and wherein the processing circuit is configured to use, when the correction data is acquired, the corrected first pattern, second pattern, name and/or variable and the text data or when the correction data is not acquired, the acquired first pattern, second pattern, name and/or variable and the text data to create metadata including pattern-specifying data that specifies one of the plurality of patterns, read a template program corresponding to each pattern specified by the pattern-specifying data, and then generate the analysis program from the template program by using the metadata.

7. The analysis program generation system according to claim 6, wherein:
the text data includes an instruction of the output format of the analysis result, and
the processing circuit is further configured to use the text date to instruct the output format of the analysis result to the template program and then generate the analysis program capable of outputting the analysis result in a layout according to the instructed output format.

8. A non-transitory computer-readable storage medium comprising a stored computer program for causing a processing circuit to execute processing in the program generation assisting system according to claim 1.

9. A non-transitory computer-readable storage medium comprising a stored computer program for causing a processing circuit to execute processing in the analysis program generation system according to claim 6.

10. A program generation assisting system for assisting generation of a program for analyzing a clinical trial, the system comprising:
a storage device configured to store a database;
an interface device configured to acquire data about an image/table analysis plan that specifies a method of analyzing the clinical trial and an output format of an analysis result; and
a processing circuit configured to output, as a candidate, a name of at least one model data to be used for analyzing the clinical trial with reference to the database and the data about the image/table analysis plan,
wherein the image/table analysis plan includes one or more forms, and each of the forms specifies analysis content for each type of analysis of the clinical trial,
wherein the database is configured to store each form of analysis materials in past clinical trials and a name of model data used in each form, namely a name of model data that is a collection of a data set and metadata for the analysis, and
wherein the processing circuit is configured to use a given similarity evaluation function to calculate, for each form of the image/table analysis plan obtained, a similarity between description in the form and description in each form of the analysis materials in the past clinical trials, extract, based on the calculated similarity, a name of at least one piece of the model data used in the form of the analysis materials in the past clinical trials, the name corresponding to the former description in the form, and then output the name of the extracted model data as the candidate.

11. The program generation assisting system according to claim 10, wherein:
the database is further configured to store link information in which the model data used in the form of the analysis materials of the past clinical trials and a variable that is an item describing the model data and used in the form are linked to each other; and
the processing circuit is configured to compare a first item of text data in each form of the image/table analysis plan with a second item of the variable of the link information, generate, in a case of match, an associated form in which the first item of the text data in each form of the image/table analysis plan and the second item of the variable of the link information are used for association, adopt, when model data having the same name of the extracted model data in the associated form, as a variable of the extracted model data, a variable that is an item describing the model data having the same name in the associated form, and then to output, in addition to the name of the extracted model data, the adopted variable as the candidate.

12. The program generation assisting system according to claim 10, wherein:
the interface device is further configured to acquire data about a model specification describing how model data prepared in the clinical trial corresponds to a definition of a variable describing the model data, and
the processing circuit is configured to calculate a degree of match between a first item of text data in each form of the image/table analysis plan and a third item indicating a variable described in the model specification by using a given algorithm, select, from the model specification, model data associated with a variable with a larger degree of match calculated than a predetermined threshold, adopt, when the selected model data matches the extracted model data, a variable larger than the threshold as a variable of the extracted model data, and then output, in addition to a name of the extracted model data, the adopted variable as the candidate.

13. The program generation assisting system according to claim 12, wherein:
the first item of text data in each form of the image/table analysis plan includes cell information of the variable, and
the third item includes label information of the variable.

14. The program generation assisting system according to claim 12, wherein:
the first item of text data in each form of the image/table analysis plan includes cell information of the variable, and
the third item includes format information indicating the variable.

15. The program generation assisting system according to claim 12, wherein:
the processing circuit is configured to extract a character string group of the first item and a character string group of the third item by an N-gram, and
calculate the degree of match based on the number of character strings common to the character string group of the first item and the character string group of the third item.

16. The program generation assisting system according to claim 15, wherein the processing circuit is configured to calculate the degree of match by using a percentage of the number of common character strings with respect to the number of all combinations of the character string group of the first item and the character string group of the third item.

17. The program generation assisting system according to claim 10, wherein the processing circuit is configured to use a given similarity evaluation function to calculate, for each form of the image/table analysis plan obtained, a similarity between description in a title of the form and description in a title of each form of the analysis materials in the past clinical trials.

18. The program generation assisting system according to claim 10, wherein the processing circuit is configured to:
generate a first vector by vectorizing, for each form in the image/table analysis plan obtained, a description of the form,
generate a second vector group by vectorizing each of a plurality of forms included in the image/table analysis plans of the past clinical trials, and
use, as the similarity evaluation function, a function that outputs a distance between each member of the first vector and each member of the second vector group to calculate the similarity.

19. The program generation assisting system according to claim 18, wherein the similarity is a Tanimoto coefficient or a Jaccard coefficient.

* * * * *